(12) United States Patent
Xiao et al.

(10) Patent No.: US 12,070,403 B2
(45) Date of Patent: Aug. 27, 2024

(54) COVERED STENT

(71) Applicant: Lifetech Scientific (Shenzhen) Co. Ltd., Guangdong (CN)

(72) Inventors: Benhao Xiao, Shenzhen (CN); Yi Fang, Shenzhen (CN)

(73) Assignee: Lifetech Scientific (Shenzhen) Co. Ltd., Guangdong (CN)

( * ) Notice: Subject to any disclaimer, the term of this patent is extended or adjusted under 35 U.S.C. 154(b) by 0 days.

(21) Appl. No.: 18/013,510

(22) PCT Filed: Jun. 4, 2021

(86) PCT No.: PCT/CN2021/098313
§ 371 (c)(1),
(2) Date: May 15, 2023

(87) PCT Pub. No.: WO2022/007560
PCT Pub. Date: Jan. 13, 2022

(65) Prior Publication Data
US 2023/0320876 A1    Oct. 12, 2023

(30) Foreign Application Priority Data

Jul. 6, 2020    (CN) .......................... 202010641395.9
Dec. 29, 2020   (CN) .......................... 202011607899.5

(51) Int. Cl.
*A61F 2/89* (2013.01)
*A61F 2/07* (2013.01)
*A61F 2/90* (2013.01)

(52) U.S. Cl.
CPC .................. *A61F 2/90* (2013.01); *A61F 2/07* (2013.01); *A61F 2/89* (2013.01)

(58) Field of Classification Search
CPC ...... A61F 2/89; A61F 2/88; A61F 2/90; A61F 2220/0058; A61F 2/07; A61F 2250/0069; A61F 2220/0075
See application file for complete search history.

(56) References Cited

U.S. PATENT DOCUMENTS

| 6,015,431 A | 1/2000 | Thornton |
| 8,163,004 B2 | 4/2012 | Amplatz |

(Continued)

FOREIGN PATENT DOCUMENTS

| CN | 1678366 | 6/2010 |
| CN | 105662666 A | 6/2016 |

(Continued)

OTHER PUBLICATIONS

Translation sections of CN 110833469 (Year: 2020).*

(Continued)

*Primary Examiner* — Brian E Pellegrino
(74) *Attorney, Agent, or Firm* — Raymond Sun

(57) ABSTRACT

A covered stent (100A), including a mesh-shaped support structure, and further including a first section (10A) and a second section (20A) connected to a proximal end and/or a distal end of the first section. The first section includes a plurality of first corrugated rings (11A), and a first covering film (12A) which covers surfaces of the first corrugated rings; the second section includes a plurality of second corrugated rings (21A), two adjacent second corrugated rings being fixedly connected to each other; a plurality of windows (201A) are formed between the plurality of second corrugated rings; and the plurality of first corrugated rings and the plurality of second corrugated rings form the support structure. The second section of the covered stent will not block an opening of a branch vessel (400), and thus it is not necessary to reduce the length of the covered stent in a main branch vessel, such that the covered stent has a sufficiently (Continued)

long anchoring area in the main branch vessel so as to ensure that the covered stent has sufficient anchoring force and thus prevent the displacement or endoleak of a distal end of the covered stent, thereby ensuring a good occluding effect.

18 Claims, 14 Drawing Sheets

(56) References Cited

U.S. PATENT DOCUMENTS

| | | | |
|---|---|---|---|
| 8,591,782 | B2 | 11/2013 | Nakayama et al. |
| 2012/0191177 | A1 | 7/2012 | Costa |
| 2016/0030218 | A1 | 2/2016 | Kasparzk |
| 2019/0175327 | A1 | 6/2019 | Xiao |
| 2020/0383769 | A1 | 12/2020 | Xiao et al. |

FOREIGN PATENT DOCUMENTS

| | | | | |
|---|---|---|---|---|
| CN | 105853033 | A | 8/2016 | |
| CN | 109069258 | | 12/2018 | |
| CN | 110833469 | A | 2/2020 | |
| EP | 686379 | A2 * | 12/1995 | ............... A61F 2/07 |
| EP | 2196175 | A1 * | 6/2010 | ............... A61F 2/89 |

OTHER PUBLICATIONS

Office Action dated Apr. 25, 2022 for corresponding China Application No. 202010641395.9 and Translation.
Response to Office Action dated Apr. 25, 2022 for corresponding China Application No. 202010641395.9 and Translation.
Observation dated Sep. 26, 2022 for corresponding China Application No. 202010641395.9 and Translation.
Notice of Grant dated Oct. 13, 2022 for corresponding China Application No. 202010641395.9 and Translation.
International Search Report dated Sep. 9, 2021 for corresponding PCT Application No. PCT/CN2021/098313.

* cited by examiner

COVERED STENT

TECHNICAL FIELD

The present invention relates to the technical field of medical instruments, and specifically to a covered stent.

BACKGROUND ART

Arterial stenosis or dissection is a disease with high mortality and high disability at present. Traditional surgery causes large traumas, many complications, and high mortality. At present, endovascular repair is often used to implant vascular stents to treat such vascular diseases. Generally, a vascular stent is delivered to a target blood vessel through a delivery device, and the stent is released and expanded to reconstruct the blood vessel or occlude a dissection rupture, so as to achieve the treatment. The endovascular repair for the vascular stent has the following advantages: small traumas, fewer complications, high safety, less pain that a patient has to suffer, less hemorrhage during the operation, shorter hospital stay, and a low-risk measure that is beneficial to the elderly in serious conditions. Usually, in order to isolate a rupture without affecting the blood supply of important branch vessels, one or more "chimney" stents are released between an aortic covered stent and an inner wall of the aorta to form a blood flow channel for the important branch vessels. This can not only ensure that the aortic covered stent covers a rupture of an aortic dissection or isolates a tumor lumen of the aorta, but also does not cover openings of the important branch vessels.

Due to the small size of the entire "chimney" stent (generally, a lumen stent is no more than 20 mm), the current "chimney" stent is usually formed by cutting or weaving. During cutting of a stent, a fiber laser is generally used to perform laser cutting on a nickel-titanium tubular material. A shape required by the stent is achieved by polishing, and shaping carried out twice or shaping carried out for multiple times. However, such a stent has the defects of stress concentration, poor fatigue performance, incapability of cutting a large-diameter product (the dimension is limited), easy breakage, and the like. During weaving of a stent, a mold is generally used to weave and shape a nickel-titanium wire-like material. Such a stent has the following disadvantages: In order to ensure the support performance of the stent, head and tail ends of a main body of the stent are generally intertwined or hooked with each other. After a product is assembled in a sheath tube, and the sheath tube is then pushed out, there is a risk of entanglement of the head and tail ends of a support body or the overall shortening of the stent, which often leads to a failure of normal spreading of the stent, or a failure of completely covering a preoperative target position, resulting in an operation failure.

In addition, due to different developments of human blood vessels, the current "chimney" stent still has some shortcomings in application:

In order to be able to effectively isolate a diseased region, a woven covered stent is usually used as a "chimney" stent. However, if an important main branch vessel has a secondary branch vessel, in order to avoid the covered stent from blocking an opening of the secondary branch vessel, an implantation depth of the covered stent in the important main branch vessel is often reduced, that is, a length of an anchoring area at a distal end of the covered stent is reduced, which will bring about the problem of insufficient anchoring force of the stent, and further lead to the displacement or endoleak of the distal end of the chimney stent, resulting in poor occluding effect.

In addition, as shown in FIG. 14, for a woven bare stent section 102, there is no connecting point between the two corrugated rings 1021 and 1022, and the two corrugated rings are in a free state. When a relative external force is applied between the corrugated rings, dislocation will occur, and the dislocation distance is a, $0 \leq a \leq h$ (h is a wave height of a single corrugated ring), that is, the bare stent section 102 is shortened, so that the anchoring area of the bare stent section is not sufficient.

SUMMARY OF THE INVENTION

For the above problems, the present invention aims to provide a covered stent. When the covered stent is implanted into a main branch vessel, the covered stent can have a sufficient anchoring length, without blocking an opening of the branch vessel. The purpose is realized by the following technical solution.

An embodiment of the present invention provides a covered stent, including a mesh-shaped support structure, and further including a first section and a second section connected to a proximal end and/or a distal end of the first section. The first section includes a plurality of first corrugated rings, and a first covering film which covers surfaces of the first corrugated rings; the second section includes a plurality of second corrugated rings, two adjacent second corrugated rings being fixedly connected to each other; a plurality of windows are formed between the plurality of second corrugated rings; and the plurality of first corrugated rings and the plurality of second corrugated rings form the support structure.

In one embodiment, the second section includes a hollow stent section; the hollow stent section includes a plurality of hollow structures; edges of the hollow structures are consistent with waveform edges of the second corrugated rings; and the hollow structures form the windows.

In one embodiment, two adjacent second corrugated rings are fixedly connected through a connector.

In one embodiment, a surface of each second corrugated ring is wrapped with a protecting film; the connectors and the protecting films both include macromolecular materials; and the connectors are fused with the protecting films.

In one embodiment, the covered stent includes a sealing structure; the sealing structure is arranged at a distal part of the first section; and the sealing structure at least partially protrudes from an outer surface of the first section.

In one embodiment, the second section further includes a second covering film; the second covering film covers surfaces of the plurality of second corrugated rings; the plurality of second corrugated rings are fixedly connected through the covering film; the second covering film is provided with a plurality of through holes; and the through holes form the windows.

In one embodiment, the second covering film includes an outer-layer covering film and an inner-layer covering film; the outer-layer covering film and the inner-layer covering film are fused into a whole via thermal treatment, and the second corrugated rings are fixed between the outer-layer covering film and the inner-layer covering film.

In one embodiment, the covered stent further includes a third section; the third section is positioned outside and surrounds the first section; a distal end of the third section is connected to the outer surface of the first section; a proximal end of the third section forms an opening facing the proximal end; and the third section includes a third corrugated ring and a third covering film covering a surface of the third corrugated ring.

In one embodiment, a corrugated ring diameter of the third corrugated ring is greater than a diameter of each first corrugated ring, and a waveform structure of the first corrugated ring is substantially the same as that of the third corrugated ring; and the wave number of the first corrugated ring is less than that of the third corrugated ring.

In one embodiment, a proximal corrugated ring of the third section and the first corrugated ring which is radially opposite to the proximal corrugated ring on the first section have crests that are staggered.

The present invention provides a covered stent, including:
a main body part, which is internally hollowed and has openings at two ends; and
a skirt part, where the skirt part is positioned outside and surrounds an outer side of the main body part; the skirt part includes a folding section and a connecting section; one end of the connecting section is connected with the main body part and forms an opening facing a proximal end; the folding section includes a connecting end; the connecting end of the folding section is connected to the other end of the connecting section, and the other end of the folding section opposite to the connecting end forms a free end; in a natural state, the folding section extends toward a distal end and forms an opening facing the distal end together with the connecting section; the folding section includes a first support member, and a fourth covering film arranged on the first support member and connected to the first support member; and an average amount of circumferential coverage of the fourth covering film close to the free end is less than that which is close to the connecting end.

In one embodiment, the thickness of the fourth covering film close to the free end is less than that of the fourth covering film close to the connecting end.

In one embodiment, the thickness of the fourth covering film gradually decreases along a direction from the connecting end of the folding section to the free end.

In one embodiment, the first support member and the fourth covering film are on the same plane; the first support member includes a plurality of support rods; among the plurality of support rods, one end of each of two adjacent support rods away from the connecting section is connected to form the free end, and the enclosed area between two adjacent support rods is larger than the area of the fourth covering film located between the two adjacent support rods.

In one embodiment, in a longitudinal extending direction of the folding section, the length dimension of the first support member is greater than that of the fourth covering film; and the free end of the first support member is exposed to the outside.

In one embodiment, each support rod includes a long support rod and a short support rod; two adjacent short support rods are connected to form a low crest; two adjacent long support rods are connected to form a high crest; the lows crests and the high crests are alternately arranged; the low crests are closer to the connecting section than the high crests; the short support rods are all covered by the fourth covering film; and the long support rods are partially exposed.

In one embodiment, the first support member and the fourth covering film are not completely in the same plane; and on the fourth covering film close to the free end, at least a part of the fourth covering film is outwardly bulged or inwardly sunken relative to the plane where the first support member is located.

In one embodiment, the fourth covering film is formed after an original covering film between two adjacent support rods is spread, and the surface area of the fourth covering film is larger than that of the original covering film.

A covered stent includes:
a main body part, which is internally hollowed and has openings at two ends; and
a skirt part, where the skirt part is positioned outside and surrounds an outer side of the main body part; the skirt part includes a folding section and a connecting section; a distal end of the connecting section is connected with an outer surface of the main body part; a proximal end of the folding section is connected with a proximal end of the connecting section; the folding section includes a first support member; the connecting section includes a second support member and a covering film; the covering film is arranged on a surface of the second support member and is connected to the second support member; in a natural state, a proximal end of the first support member is connected to a proximal end of the second support member; a distal end of the first support member extends towards the distal end to form a free end; and the covering film extends from the distal end of the second support member to the proximal end of the second support member and does not exceed the proximal end of the first support member.

In one embodiment, in the natural state, a projection of the free end of the folding section on the outer surface of the main body part overlaps a connecting point between the connecting section and the outer surface of the main body part, or a projection of the free end of the folding section on the outer surface of the main body part is closer to the proximal end of the main body part than the connecting point between the connecting section and the outer surface of the main body part.

According to the embodiments of the present invention, the covered stent includes the first section and the second section connected to the distal end of the first section. After the covered stent is implanted into a main branch vessel, the covered stent can form a blood flow channel of the main branch vessel. If there are secondary branch vessels on the main branch vessel, after the covered stent is implanted, the second section covers an opening of the secondary branch vessel, but due to the windows formed in the second section, the second section does not block a passage of blood from the main branch vessel to the secondary branch vessel. It can be seen that the second section of the covered stent of the embodiments of the present invention will not block the opening of the secondary branch vessel, and thus it is not necessary to reduce the length of the covered stent in a main branch vessel, such that the covered stent has a sufficiently long anchoring area in the main branch vessel so as to ensure that the covered stent has sufficient anchoring force and thus prevent the displacement or internal leakage of a distal end of the covered stent, thereby ensuring a good occluding effect.

According to the covered stent of the present invention, when it is necessary to connect the window of a main body stent in a blood vessel, the distal end of the main body part of the covered stent extends to the outside of the main body stent through the window. As the main body part penetrates, the folding section of the skirt part is in contact with an inner wall of the window. Since the average amount of circumferential coverage of the fourth covering film close to the free end is less than that which is close to the connecting end, or the covering film extends from the distal end of the second support member to the proximal end of the second support member and does not exceed the proximal end of the first support member, the folding section can be easily folded, and thus, the skirt part completes automatic flipping under extrusion of an external force after being shaped, which effectively ensures the success rate of positioning of the stent in an operation.

BRIEF DESCRIPTION OF THE DRAWINGS

The accompanying drawings are only used for the purpose of illustrating the preferred implementation modes, and are not considered as a limitation to the present invention. Furthermore, throughout the drawings, the same reference numerals are used to denote the same components. In the drawings.

Figure 1:
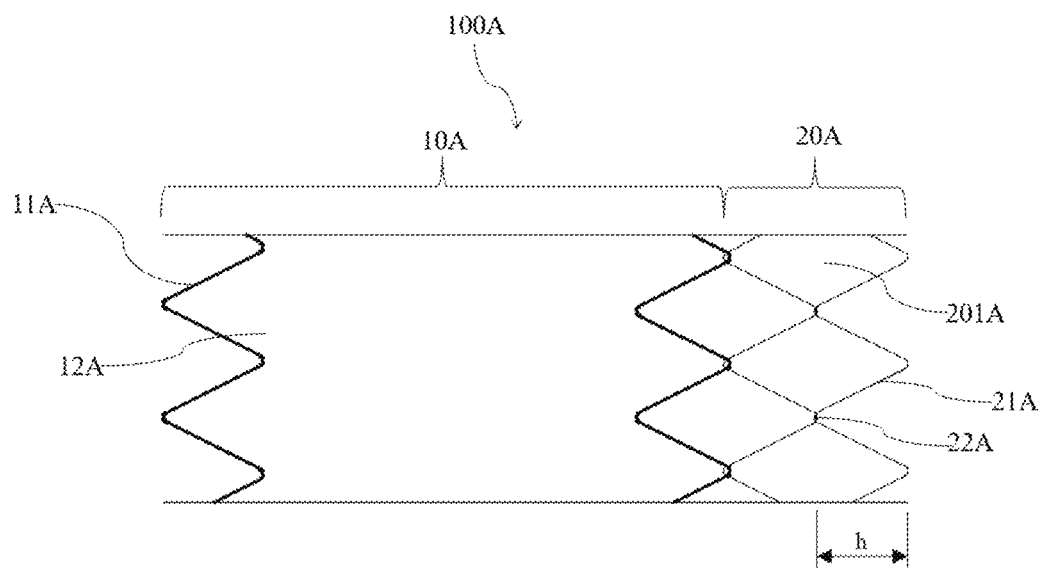
FIG. 1 is a schematic structural diagram of a covered stent according to one embodiment of the present invention.

It should be noted that the drawings of the present invention only show some support members for illustration, and the support members are not the main focus of the present invention. Those skilled in the art can select and design the specific structures and parameters of the support members according to actual needs.

DETAILED DESCRIPTION OF THE INVENTION

Exemplary implementations of the present invention will be described in more detail below with reference to the accompanying drawings. Although the exemplary implementations of the present invention are shown in the drawings, it should be understood that the present invention can be implemented in various forms and should not be limited by the implementations set forth herein. On the contrary, these implementations are provided to enable a more thorough understanding of the present invention and to fully deliver the scope of the present invention to those skilled in the art.

It should be understood that the terms used herein are only for the purpose of describing specific example implementation modes, and are not intended to be limitations. Unless the context clearly indicates otherwise, the singular forms "a", "an" and "said" as used in the text may also mean that the plural forms are included. The terms "comprise", "include", "contain" and "has" are inclusive and therefore indicate the existence of the stated features, steps, operations, elements and/or components, but do not exclude the existence or addition of one or more of other features, steps, operations, elements, components, and/or combinations thereof. The method steps, processes, and operations described herein are not interpreted as requiring them to be executed in a specific order described or illustrated, unless the order of execution is clearly indicated. It should also be understood that additional or alternative steps may be used.

Although the terms first, second, third, etc. may be used in the text to describe multiple elements, components, regions, layers and/or sections, these elements, components, regions, layers and/or sections should not be restricted by these terms. These terms may only be used to distinguish one element, component, region, layer or section from another region, layer or section. Unless the context clearly indicates otherwise, terms such as "first", "second" and other numerical terms do not imply an order or a sequence when used in the text. Thus, a first element, component, region, layer or section discussed below could be referred to as a second element, component, region, layer or section without departing from the teachings of example implementations.

For ease of description, spatially relative terms may be used herein to describe a relationship of one element or feature to another element or feature as shown in the figures, such as "inner", "outer", "inside" ", "outside", "below", "under", "over", "above", etc. This spatially relative term is intended to include different orientations of a device in use or operation other than the orientation depicted in the figures. For example, if the device in the figures flips over, elements described as being "below or under other elements or features" would then be oriented as being "over or "above other elements or features". Thus, the example term "below" can include both upper and lower orientations. The device may be otherwise oriented (rotated 90 degrees or in other orientations) and is correspondingly interpreted with the spatially relative descriptors used herein.

In order to describe the structure of the present application more clearly, the terms "proximal end" and "distal end" are defined herein as commonly used terms in the field of medical instruments. Specifically, "distal end" means an end where blood flows out, and "proximal end" means an end where blood flows in. In the present invention, blood flows in from a proximal end of a covered stent and flows out from a distal end of the covered stent; "axial direction" means a lengthwise direction of the covered stent, and "radial direction" means a direction perpendicular to the "axial direction".

The covered stent of the present invention can be used in conjunction with the main body stent implanted in an aorta, thereby reconstructing a blood supply of a branch vessel.

Embodiment I

As shown in FIG. 1, one of the embodiments of the present invention provides a covered stent 100A. The covered stent 100A includes a first section 10A, and a second section 20A connected to a distal end of the first section 10A. The first section 10A includes a plurality of first corrugated rings 11A, and a first covering film 12A which covers surfaces of the first corrugated rings 11A. The second section 20A includes a plurality of second corrugated rings 21A; a plurality of windows 201A are formed between the plurality of second corrugated rings 21A; and the plurality of windows 201A can allow blood to flow therethrough. The plurality of first corrugated rings 11A and the plurality of second corrugated rings 21A both constitute a mesh-shaped support structure.

The covered stent 100A according to this embodiment of the present invention includes the first section 10A, and the second section 20A connected to the distal end of the first section 10A. After the covered stent 100A is implanted into a main branch vessel, the covered stent 100A can form a blood flow channel of the main branch vessel. Since the covered stent requires a certain anchoring force after being implanted into a blood vessel, certain requirements will be put forward on the length of the covered stent (for example, the length is not less than 15 mm). If there is a secondary branch vessel at a position that is close to an opening of the main branch vessel, after the covered stent 100A is implanted, the second section 20A covers the opening of the secondary branch vessel. Since the windows 201A are formed on the second section 20A, the second section 20A will not block a passage of the blood from the main branch vessel to the branch vessel. It can be seen that the second section 20A of the covered stent 100A according to the embodiments of the present invention does not block the opening of the branch vessel. Therefore, it is not necessary to reduce the length of the covered stent 100A in the main branch vessel, such that the covered stent 100A has a sufficiently long anchoring area in the main branch vessel so as to ensure that the covered stent 100A has sufficient anchoring force, and thereby prevent the displacement or endoleak of the distal end of the covered stent 100A, thereby ensuring a good occluding effect, without affecting the blood supply of the secondary branch vessel.

Figure 2:
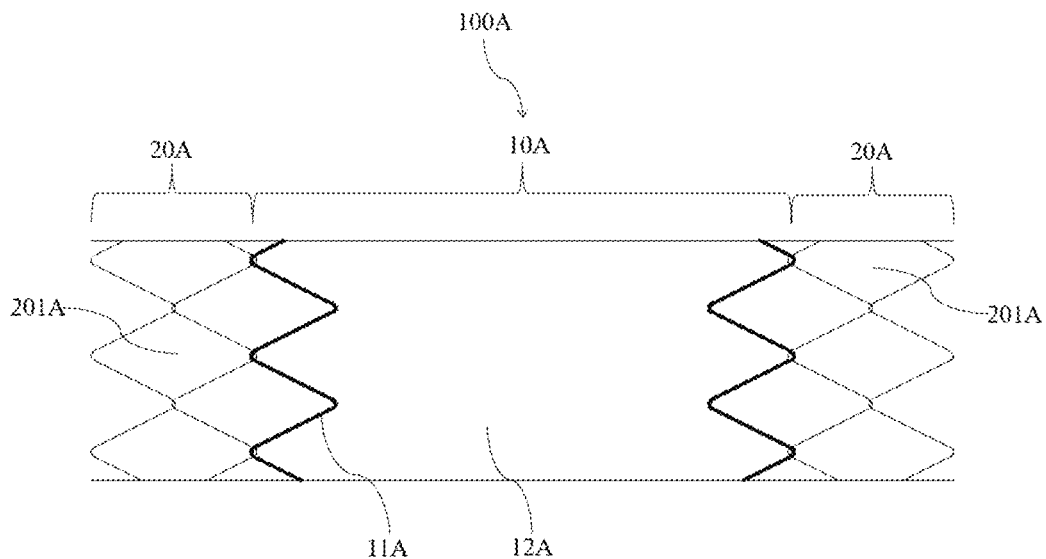
FIG. 2 is a schematic structural diagram of a covered stent according to another embodiment of the present invention.
Figure 14:
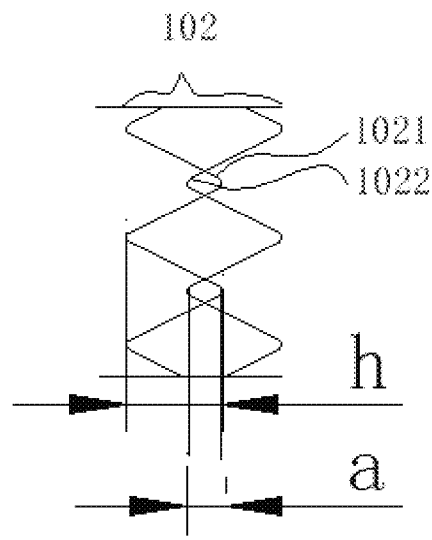
FIG. 14 is a schematic structural diagram showing a corrugated ring structure of the prior art after it is shortened.

It can be understood that, in the above embodiment, the second section 20A is connected to the distal end of the first section 10A. In other embodiments, the second section 20A can also be connected to the proximal end of the first section 10A. For example, when the covered stent of the present invention partially covers the openings of other adjacent main branch vessels on the aortic vessel after implantation, since the second section is disposed at the proximal end of the first section and the second section is provided with the windows, the second section will not block the blood from flowing into the adjacent main branch vessel. Alternatively, both the distal end and the proximal end of the first section 10A are both connected with the second sections 20A (as shown in FIG. 2), so that the covered stent has sufficient anchoring force in the main branch vessel, and at the same time, will neither block the opening of the secondary branch vessel on the main branch vessel, nor block the opening of the adjacent main branch vessel. Specifically, a selection can be made according to the actual development (a location where the branch vessel is located) of a blood vessel. The above several situations all fall within the protection scope of the present invention.

In this embodiment, the first covering film 12A can be made of polytetrafluoroethylene (PTFE) material, and includes an inner-layer covering film and an outer-layer covering film. The outer-layer covering film and the inner-layer covering film can be fused into a whole via thermal treatment, so as to fix the first corrugated ring 11A between the outer-layer covering film and the inner-layer covering film. As shown in FIG. 1, both ends of the first covering film 12A are designed in a "petal-like" structure, that is, the two ends of the first covering film 12A are wavy, and a wavy undulating edge is consistent with the waviness of the first corrugated rings 11A.

As shown in FIG. 1, the second section 20A includes a hollow stent section. The hollow structure on the hollow stent section forms the windows 201A, and the hollow structure can allow the blood to freely pass. Therefore, when the hollow stent section covers the opening of the secondary branch vessel, the blood can freely flow from the main branch vessel to the secondary branch vessel through the hollow structure.

Figure 3A:
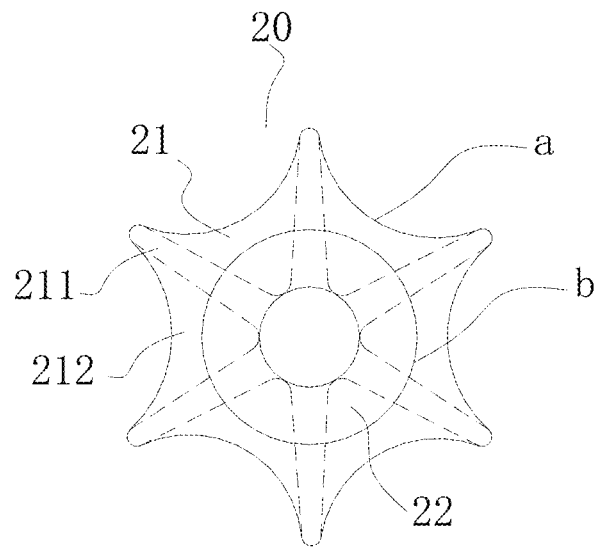
FIG. 3A is a schematic structural diagram of a covered stent according to another example in Embodiment VI.
Figure 3:
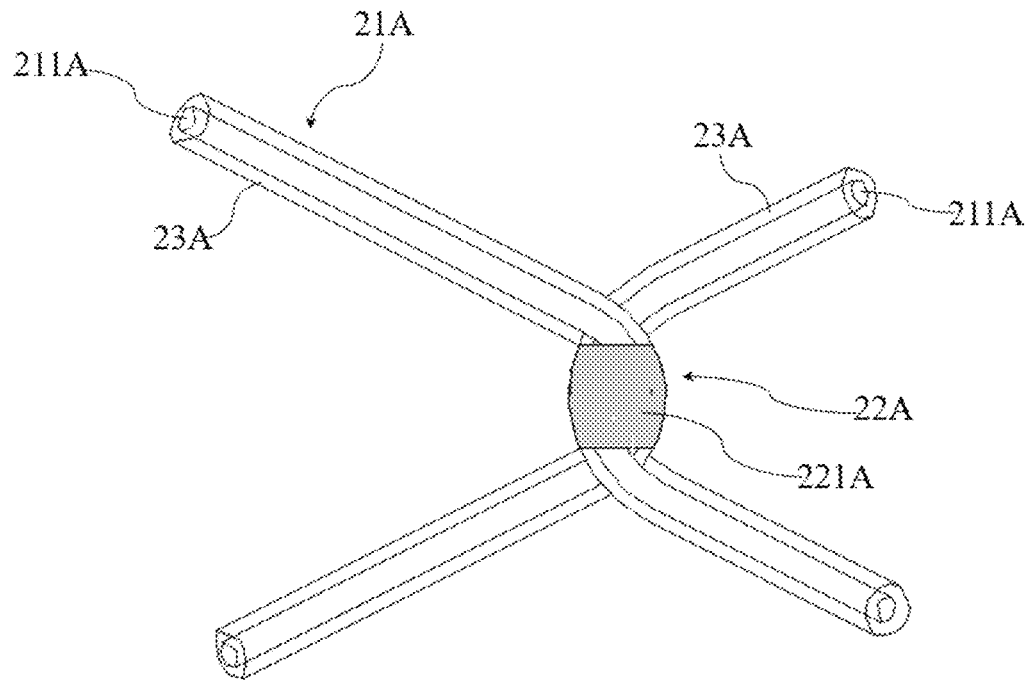
FIG. 3 is a schematic diagram of the connection of two adjacent second corrugated rings according to one embodiment of the present invention.

Referring to FIG. 1 and FIG. 3 at the same time, the hollow stent section includes a plurality of second corrugated rings 21A, and two adjacent second corrugated rings 21A are fixedly connected by connectors 22A. When the second section 20A is pulled by an external force (e.g., the impact of the blood flow, an external force when the covered stent 100A is released through a delivery device, etc.), the connectors 22A can resist the impact of the external force, so that two adjacent two second corrugated rings 21A will not be dislocated, thereby ensuring that the hollow stent section will not be shortened, and ensuring that the length of the anchoring area of the covered stent 100A will not be shortened so as to maintain the sufficient anchoring force. In this embodiment, a wave height of the second corrugated ring 21A is h. The range of the wave height h is 2.5 mm≤h≤5.0 mm.

Figure 4:
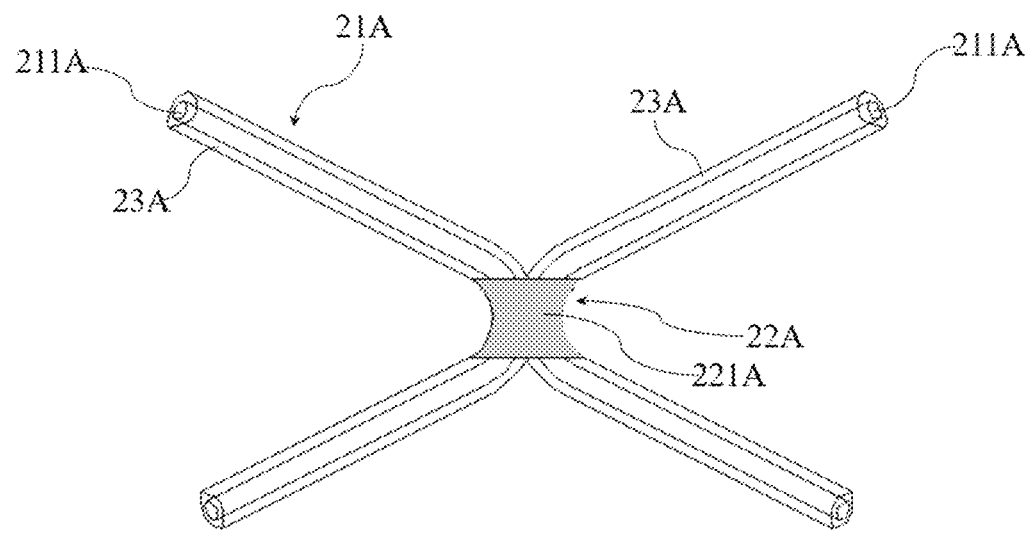
FIG. 4 is a schematic diagram of the connection of two adjacent second corrugated rings according to another embodiment of the present invention.

The connection between two adjacent second corrugated rings 21A may be as shown in FIG. 3 and FIG. 4. That is, two adjacent second corrugated rings 21A are connected side by side. They do not overlap in a radial direction of the covered stent, and are then directly fixed by the connectors. Alternatively, two connected second corrugated rings 21A are connected by way of mutual hanging. The crest of one second corrugated ring is connected to the trough of the other second corrugated ring. In this embodiment, a surface of a metal wire 211A of the second corrugated ring 21A is wrapped with a protecting film 23A made of a highly biocompatible macromolecular material. Compared with the metal wire, the protecting film 23A causes less stimulation to a blood vessel. The connector 22A fixedly connects two adjacent second corrugated rings 21A in a winding manner, and the connector 21A and the protecting film 23 are fused together. The connector 22A can be made of a macromolecular material, and can be a wire or a strip. In this embodiment, both the connector 221A and the protecting film 23A can be made of a PTFE film.

Figure 5A:
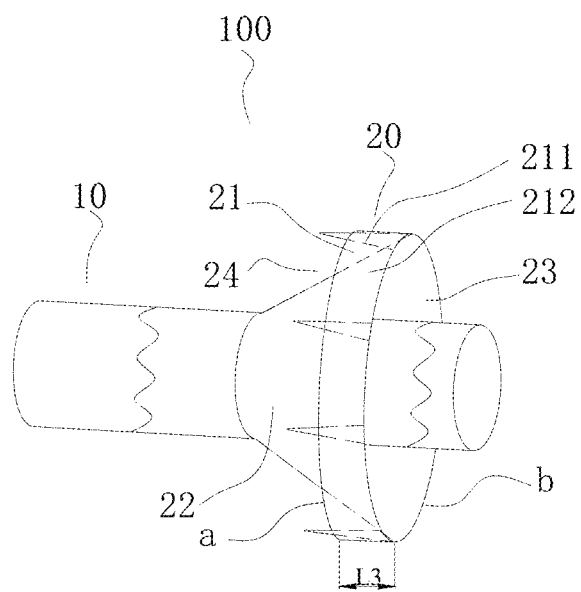
FIG. 5A is a schematic structural diagram of a covered stent of Embodiment VII in a natural state.
Figure 5:
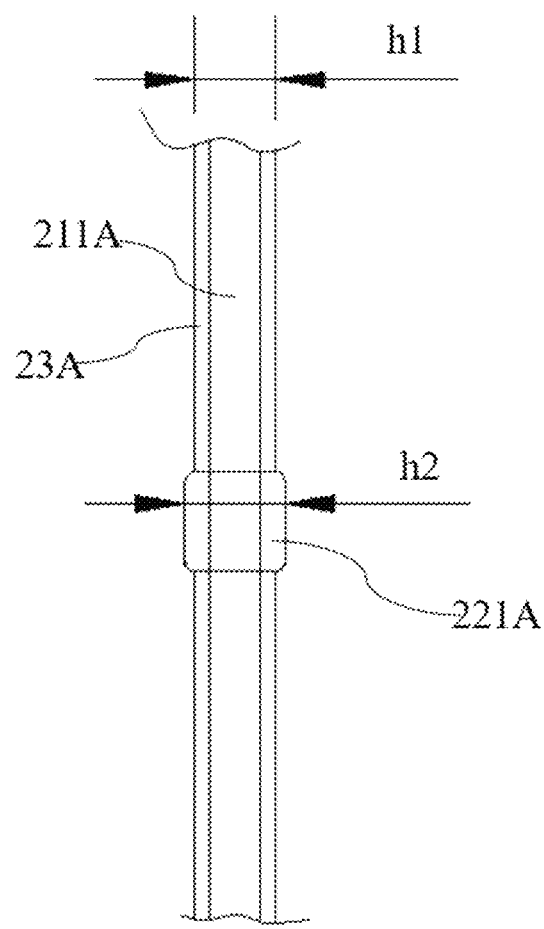
FIG. 5 is a schematic diagram of the connection between a connector and a metal wire of a second corrugated ring according to one embodiment of the present invention.

As shown in FIG. 5, the connector 22A may be wound on the second corrugated ring 21A multiple times, so that the connector 22A radially protrudes from a surface of the second section 20A. As a result, the anchoring force between the second section 20A and the blood vessel can be improved. In addition, the increase in the number of layers of winding can also improve the connection stability between two adjacent second corrugated rings 21A, thereby improving the capability of resisting the external impact. Specifically, the number of layers of winding of the connector 221A can be controlled between 4 and 10. Generally speaking, the thickness of one layer of film is about 0.1 mm, so that the dimension at the connector 22A is h2=h1+0.1*n, where h1 is the sum of a wire diameter of the metal wire of the second corrugated ring 21 and the thickness of the protecting film, and n is the number of layers of winding, which can be equal to any integer between 4 and 10.

It can be understood that, in other embodiments, the connector 22A may also be of a welded structure or a metal wire wound on two adjacent second corrugated rings 21A. In other words, two adjacent second corrugated rings 21A can be wound together by a metal wire, or can also be directly connected by welding, so as to realize the connection between the two adjacent second corrugated rings 21A.

As shown in FIG. 3, two adjacent second corrugated rings 21A are connected in a mutually hooked manner. By the cooperation with the connector 22A, a stable connection can be achieved between the two adjacent corrugated rings 21A. In addition, this connection method is favorable for forming a protruding structure at a connection position, so as to improve the anchoring force between the second section 20A and the blood vessel.

As shown in FIG. 4, in some other implementations, two adjacent second corrugated rings 21A may also be abutted to contact each other, and are then connected by the connector 22A. On this basis, the connection stability between the second corrugated rings 21A can also be improved by increasing the number of layers of winding of the connector 221A, and the connector 22A can protrude from the surface of the second section 20A.

In order to facilitate the machining, and to minimize the machining time of the covered stent, the plurality of first corrugated rings and the plurality of second corrugated rings can be integrally woven. For example, the crests and troughs of the first corrugated rings and the second corrugated rings are connected in the mutually hooked manner by means of weaving the metal wires, and the first corrugated rings and the second corrugated rings are further covered with films or subjected to other treatments respectively. By adopting this mutually hooked weaving method, the connection force between the corrugated rings is higher, and the overall support performance of the covered stent is better.

Figure 6:
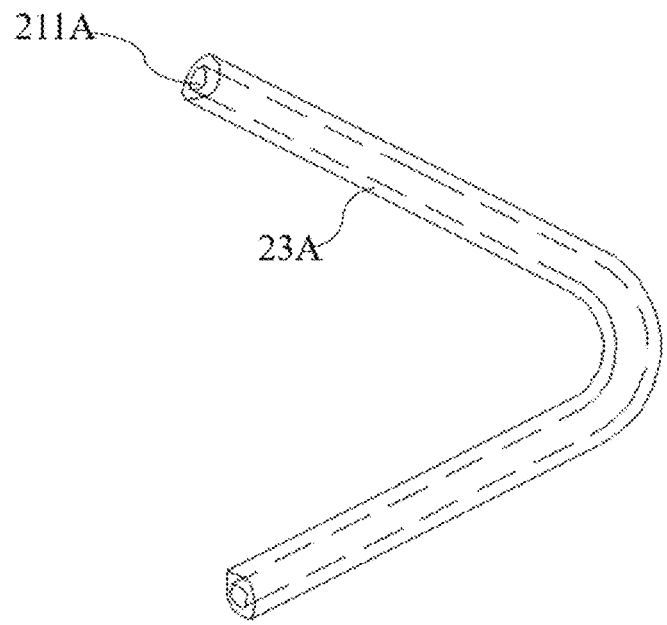
FIG. 6 is a schematic diagram of a method of forming a protecting film according to one embodiment of the present invention.
Figure 7:
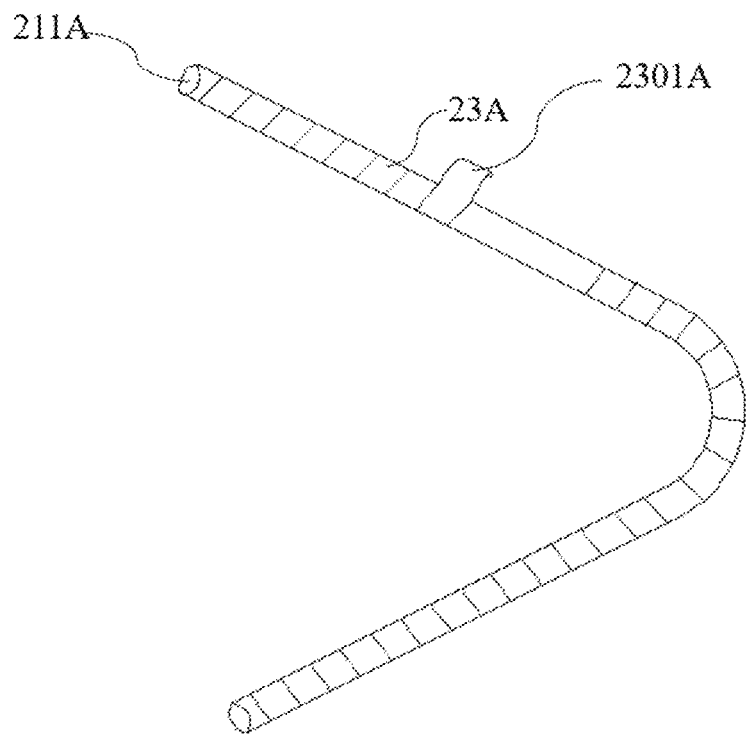
FIG. 7 is a schematic diagram of a method of forming a protecting film according to another embodiment of the present invention.

There may be 1 to 3 layers of protecting films 23A wrapped on the surface of the metal wire 211A of the second corrugated ring 21A. The protecting film may be formed by sleeving an entire film on the surface of the metal wire 211A (as shown in FIG. 6), and may also be formed by winding a narrow bar film 2301A on the surface of the metal wire 211A (as shown in FIG. 7). After the thermal treatment, the protecting film 23A is attached to the surface of the metal wire 211A.

Since the second section 20A is a hollow stent section, wrapping the highly biocompatible protecting film 23A on the surface of the metal wire 211A of the 20A can improve the biocompatibility of the second section 20A. The protecting film 23A may be fixed on the surface of the metal wire 211A via thermal treatment. In another aspect, two adjacent second corrugated rings 21A are fixed by the connector 22A in a winding manner. Furthermore, the connector 22A and the protecting film 23A wrapped on the surface of the metal wire 221A are fused together via thermal treatment. Thus, stable connection is formed between two second corrugated rings 21A, so as to resist the impact of the external force and ensure that no dislocation occurs between the two second corrugated rings 21A.

Figure 8:
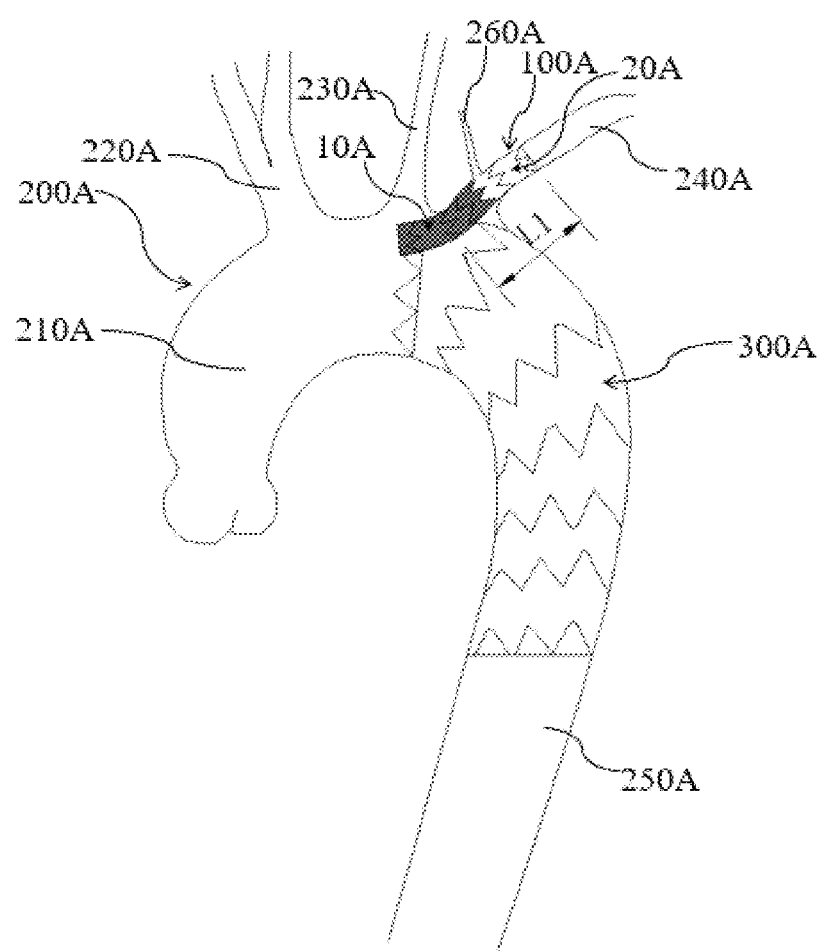
FIG. 8 is a schematic diagram showing the release of a covered stent in an aortic arch vessel according to one embodiment of the present invention.

A method of use and the effects of the covered stent of the present invention will be described below with two specific embodiments:

FIG. 8 is a schematic diagram showing the release of a covered stent 100A in an aortic arch vessel 200A according to one embodiment. The aortic arch vessel 200A includes an ascending aortic vessel 210A, a brachiocephalic artery 220A, a left common carotid artery vessel 230A, a left subclavian artery 240A, and a descending aortic vessel 250A. A left vertebral artery 260A branches from the opening close to the left subclavian artery 240A. When a main body covered stent 300A is used to treat the lesion in the aortic arch vessel 200A, the blood flow channel of the left subclavian artery 240A needs to be reconstructed to ensure the blood supply of the corresponding blood vessel. The main body covered stent 300A can isolate a proximal rupture or tumor lumen of an aortic dissection, and can complete unblockage of the branch vessel by cooperating with the covered stent 100A. In order to ensure that the covered stent 100A has sufficient anchoring area after the implantation and will not move, an anchoring requirement for the left subclavian artery 240A is that the anchoring length is not less than 15 mm, that is, L1≥15 mm shown in FIG. 8. If the entire main body covered stent is used for an operation, the stent will block the opening of the left vertebral artery 260A, resulting in ischemia of the left upper limb and corresponding complications. When the covered stent 100A of the present invention is used for treatment, the main body covered stent 300A is first released to a designated position, and the covered stent 100A is then positioned, and an appropriate specification is selected so that the first section 10A is flush with an edge of the opening in the proximal end of the main body covered stent 300A (the proximal end of the covering film on the first section 10A is closer to the heart than the proximal end of the covering film on the main body covered stent 300A). The proximal end of the second section 20A is closer to the proximal end of the main body covered stent 300A than the opening of the left vertebral artery 260A, that is, the second section 20A can cross the opening of the left vertebral artery 260A to keep the blood unblocked.

In this embodiment, the first section 10A of the covered stent 100A is attached with the first covering film 12A, thereby avoiding endoleak of the proximal end. The windows are formed in the second section 20A, which can prevent the opening of the left vertebral artery 260A from being blocked. The anchoring area of the covered stent is long enough to also satisfy the anchoring condition (L1≥15 mm) and prevent the stent from moving.

Figure 9A:
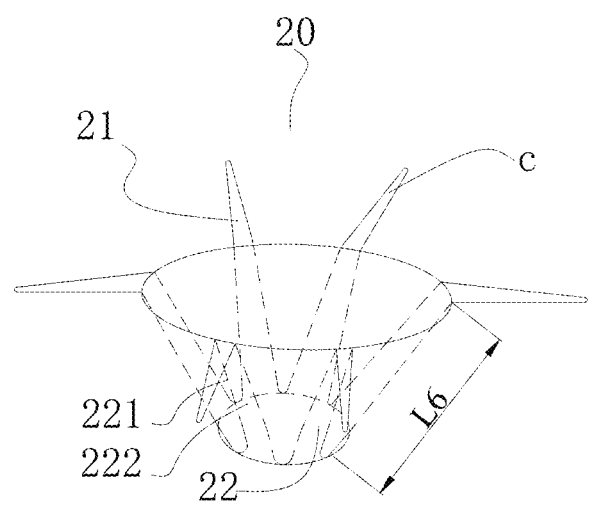
FIG. 9A is a schematic structural diagram of a skirt part, in which a folding section of the covered stent in FIG. 8A is in a folding state.
Figure 9:
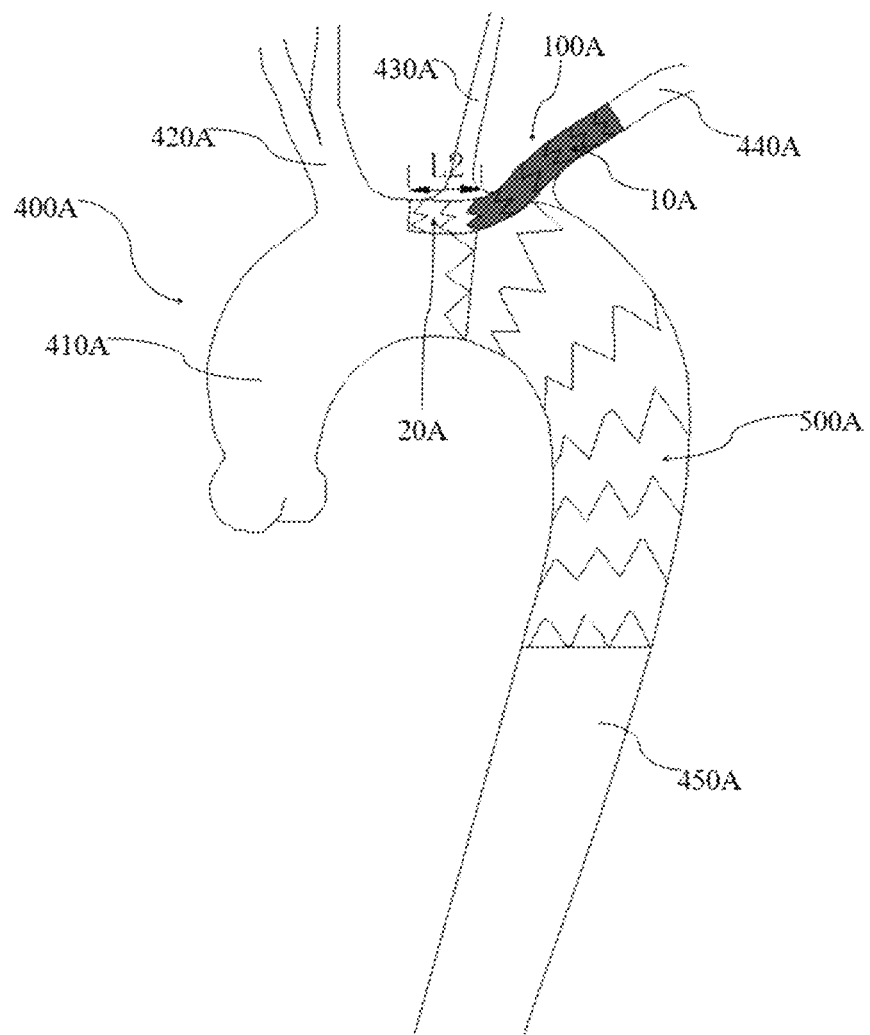
FIG. 9 is a schematic diagram showing the release of a covered stent in an aortic arch vessel according to another embodiment of the present invention.

FIG. 9 is a schematic diagram showing the release of a covered stent 100A in an aortic arch vessel 400A according to another embodiment of the present invention. One difference from the previous embodiment is that the covered stent 100A is released in a reverse manner, and the proximal end and distal end of the covered stent 100A are transposed. The aortic arch vessel 400A includes an ascending aortic vessel 410A, a brachiocephalic artery 420A, a left common carotid artery vessel 430A, a left subclavian artery 440A, and a descending aortic vessel 450A. The distance between the openings of the left subclavian artery 440A and the left common carotid artery vessel 430A is within 10 mm. In order to treat an aortic dissection or aortic aneurysm in the aortic arch vessel 400A, it is necessary to reconstruct a blood flow channel of the left subclavian artery 440A. A main body covered stent 500A can be used to isolate a proximal rupture or a tumor lumen of the aortic dissection, and complete the reconstruction of the blood flow of the branch vessel by cooperating with the covered stent 100A. When it is ensured that the anchoring length of the distal end of the left subclavian artery 440A is not less than 15 mm, the anchoring length of the proximal end of the covered stent is also required to be not less than 15 mm, that is, L2≥15 mm shown in the figure. If a fully covered stent is used for an operation, since the distance between the openings of the left subclavian artery 440A and the left common carotid artery vessel 430A is small, the covered stent will block the opening of the left common carotid artery vessel 430A, causing cerebral ischemia, resulting in corresponding complications. When the covered stent 100A of the present invention is used for treatment, the main body covered stent 500A is first released to a designated position, and the appropriate covered stent 100A is selected, so that the proximal end of the first section 10A is flush with an edge of the covering film of the opening in the proximal end of the main body covered stent 500A, which can prevent endoleak from a gap. The second section 20A can cross the opening of the left common carotid artery vessel 430A, and the second section 20A includes a hollow section, which can keep the blood flow unblocked. The anti-retraction structure can prevent the stent from moving, and the main body covered stent 500A would not close the proximal end of the second section 20A.

In this embodiment, the first section 10A of the covered stent 100A can prevent reflux endoleak of the distal end, and the second section 20A can prevent adjacent main branch arteries from being blocked, and can also satisfy an anchoring condition (L≥15 mm) to prevent the stent from moving.

Embodiment II

Another embodiment of the present invention provides a covered stent 100A. One difference from Embodiment I is that the second section 20A of this embodiment includes a second covering film.

Specifically, the second section 20A includes a plurality of second corrugated rings 21A and a second covering film which covers surfaces of the second corrugated rings 21A. A plurality of through holes are provided on the second covering film, and the through holes form the windows 201A. In this embodiment, the second covering film and the first covering film 12A may be two parts of an entire covering film, that is, the part of the entire covering film located on the first section 10A is the first covering film 12A, and the part located on the second section 20A is the second covering film. The plurality of through holes are formed in the second covering film, and the positions of the through holes preferably avoid the second corrugated rings, so that the second corrugated rings are not directly exposed to the blood. The through hole can be used as the window 201A for allowing the blood to pass through, so that the second section 20A will not block the opening of a branch vessel. It can be understood that the through hole in the second covering film can be formed by removing part of the covering film, or by forming a cut (e.g., a cross-shaped cut) in the covering film, but still maintaining all the covering films. It should be understood that a larger through hole allows the blood to flow more easily into the secondary branch vessel.

The second covering film includes an outer-layer covering film and an inner-layer covering film; the outer-layer covering film and the inner-layer covering film are fused into a whole via thermal treatment, so as to fix the second corrugated rings 21A between the outer-layer covering film and the inner-layer covering film. Each second corrugated ring 21A is fused by the inner-layer covering film and the outer-layer covering film, so that different second corrugated rings 21A have a relatively fixed positional relationship, and there is no dislocation between adjacent second corrugated rings 21A. Therefore, the covered stent 100A is not shortened due to the action of an external force. It can be understood that the second covering film of the present invention can be equivalent to the protecting film of Embodiment I.

Embodiment III

Figure 10:
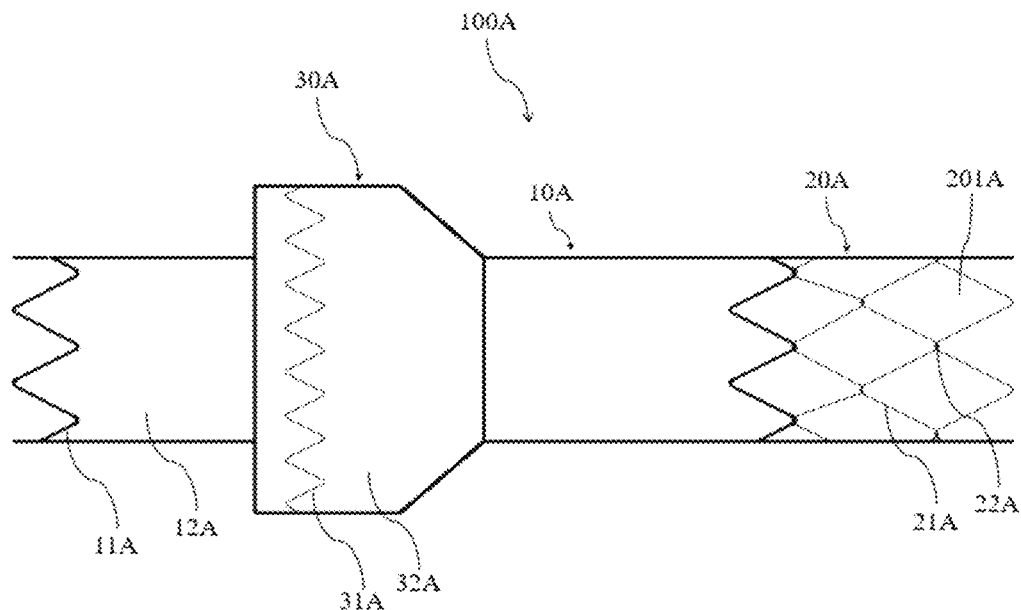
FIG. 10 is a schematic structural diagram of a covered stent according to another embodiment of the present invention.

As shown in FIG. 10, another embodiment of the present invention provides a covered stent 100A, which is substantially the same in structure as those in Embodiments I and II, except that the covered stent 100A further includes a third section 30A.

Specifically, the third section 30A includes a plurality of third corrugated rings 31A, and a third covering film 32A attached to surfaces of the third corrugated rings 31A. The third section 30A is positioned on, and surrounds, the outer surface of the first section 10A so as to form a skirt structure outside the first section 10A. A distal end of the third section 30A is connected to the outer surface of the first section 10A so as to form an opening that faces the proximal end of the first section 10A at a proximal end, and the proximal end of the third section 30A does not exceed the proximal end of the first section 10A. The covered stent 100A in this embodiment constitutes a partial double-layer covered structure, and the third section 30A can further solve the problem of endoleak of a "chimney" stent. The structures of the first section 10A and the second section 20A of the covered stent 100A are the same as those in the foregoing embodiments, and will not be repeated here. FIG. 10 only shows one third corrugated ring at the most proximal end of the third section, and the remaining third corrugated rings are not shown.

As shown in FIG. 10, an outer diameter of the third section 30A is greater than that of the first section 10A, and the waveform structure of the first corrugated ring 11A is substantially the same as that of the third corrugated ring 31A. In the present application, the structures of the two corrugated rings are substantially the same, which means that there is no significant difference in wave heights and angles of the crests and troughs in the two corrugated rings. In this embodiment, the diameter of the corrugated ring of the third section 30A is approximately twice the diameter of the first section 10A. For the corrugated rings with approximately the same waveform dimensions, a larger diameter indicates a lower radial force of the corrugated ring. Therefore, when the covered stent 100A shown in FIG. 10 is used with the main body covered stent shown in FIG. 8 or FIG. 9, the third section 30A will be extruded to greatly deform, so it can provide a better sealing effect, while the first section has a radial support effect and less deformation, so as to ensure the dimension of the opening of the proximal end of the first section and ensure that branch blood can fully flow into the covered stent 100A.

In this embodiment, in order to avoid the phenomenon that the proximal end of the third section 30A experiences difficulty in spreading after the covering film at the proximal part of the third section 30A is stuck to the covering film on the outer surface of the first section 10A, preferably, the proximal corrugated ring (i.e., the third corrugated ring 31A closest to the proximal end) of the third section 30A and the first corrugated ring (that is radially opposite to the proximal corrugated ring of the third section 30A) on the first section 10A are distributed with their crests staggered. That is, after the covered stent is compressed, the covering film between two adjacent crests on the first corrugated ring (that is opposite to the proximal corrugated ring of the third section 30A) on the first section 10A is opposite to the crest on the third section 30A. More preferably, when the wave number of the proximal corrugated ring of the third section 30A is different from the wave number of the first corrugated ring (that is radially opposite to the proximal corrugated ring of the third section 30A) on the first section 10A, the number is odd or even. The wave number is the number of crests or troughs of a single corrugated ring. In order to take into account the radial support force of the aforementioned corrugated ring, in this embodiment, the wave number of the third corrugated ring 31 of the third section 30A is greater than the wave number of the first corrugated ring 11A on the first section 10A. Preferably, the wave number of the third corrugated ring 31 ranges from 6 to 12, and the wave number of the first corrugated ring 11A ranges from 5 to 8.

It can be understood that, in order to facilitate the spreading of the third section, in other embodiments, the crest of the proximal corrugated ring of the third section may also be set as an exposed crest, that is, the crest of the proximal corrugated ring of the third section is not covered by the covering film. Therefore, when the covered stent is compressed, the exposed crest is directly in contact with the covering film on the outer surface of the first section, so that no adhesion between the covering films occurs, and the third section can spread more easily.

Embodiment IV

Figure 11:
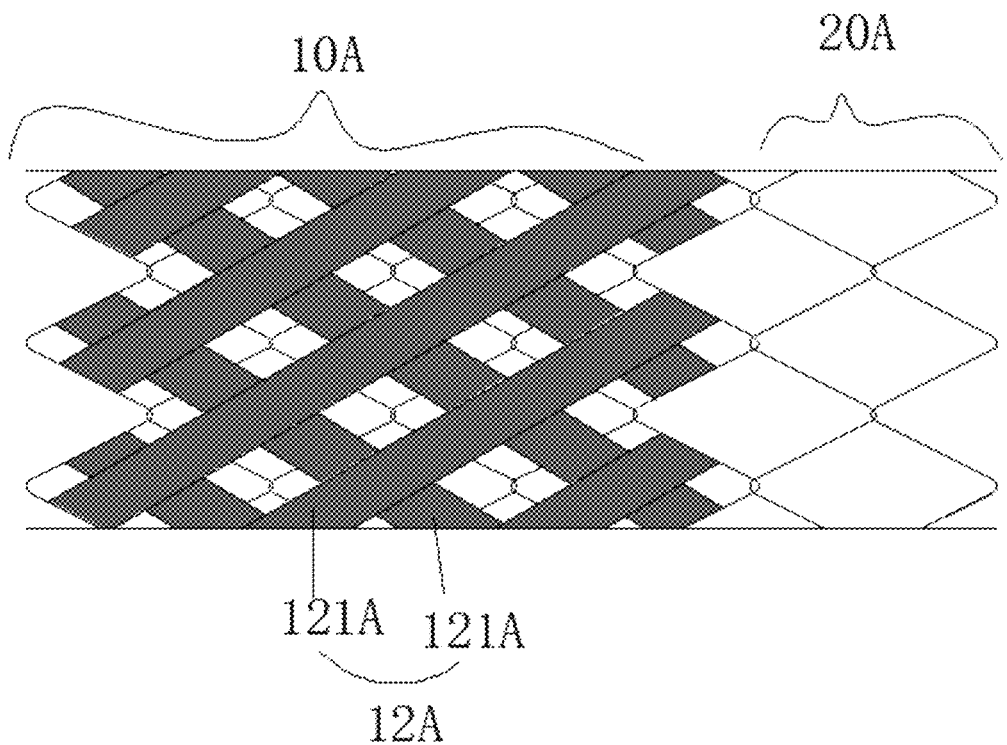
FIG. 11 is a schematic structural diagram of a covered stent according to a further embodiment of the present invention.
Figure 10A:
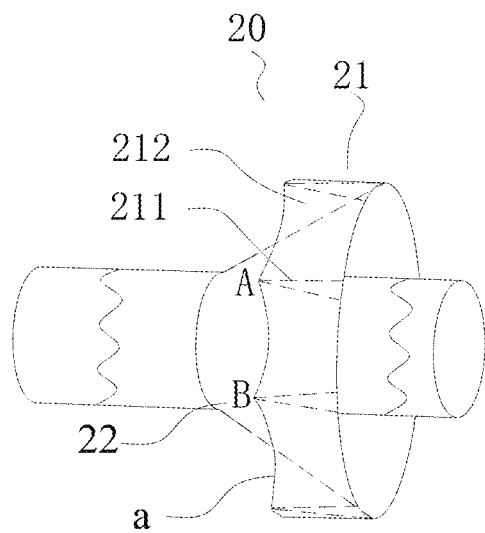
FIG. 10A is a schematic structural diagram of a covered stent of Embodiment IX in a natural state.

As shown in FIG. 11, the covered stent of this embodiment has substantially the same structure as that of the covered stent of Embodiment I, except that the outer-layer covering film of the first covering film 12A of this embodiment includes a plurality of covering film tapes 121A (the inner-layer covering film is not shown). Specifically, the plurality of first corrugated rings and the plurality of second corrugated rings of the covered stent in this embodiment are formed via integrated weaving, that is, adjacent corrugated rings are connected by hooking crests and troughs. The plurality of covering film tapes 121A are intersected with each other and form a plurality of blank regions, and the plurality of blank regions are opposite to the crest-trough hooking positions of two adjacent first corrugated rings 11A, so that outer surfaces of the crest-trough hooking positions are exposed. Therefore, two adjacent first corrugated rings can move axially relative to each other, so that the first section 10A of the covered stent can adapt to the curvature of a blood vessel. When the covered stent is implanted into the main branch vessel, the compliance is better. After the implantation, the covered stent is more stable.

The outer-layer covering film of the first section 10A of the covered stent of this embodiment completely adopts a covering film tape for covering, so that the crest-trough hooking positions of the first corrugated rings are movable, and the entire first section has better compliance. In other embodiments, partial crest-trough hooking positions are movable. For example, the movable crest-trough hooking positions of the first corrugated rings are disposed at the distal part of the second section only, or movable sections are sectionally disposed in a lengthwise direction of the first section.

Figure 12A:
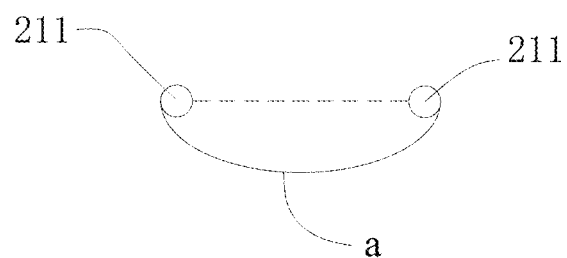
FIG. 12A is a partial schematic sectional structural diagram of a folding section of another example in Embodiment IX.
Figure 12:
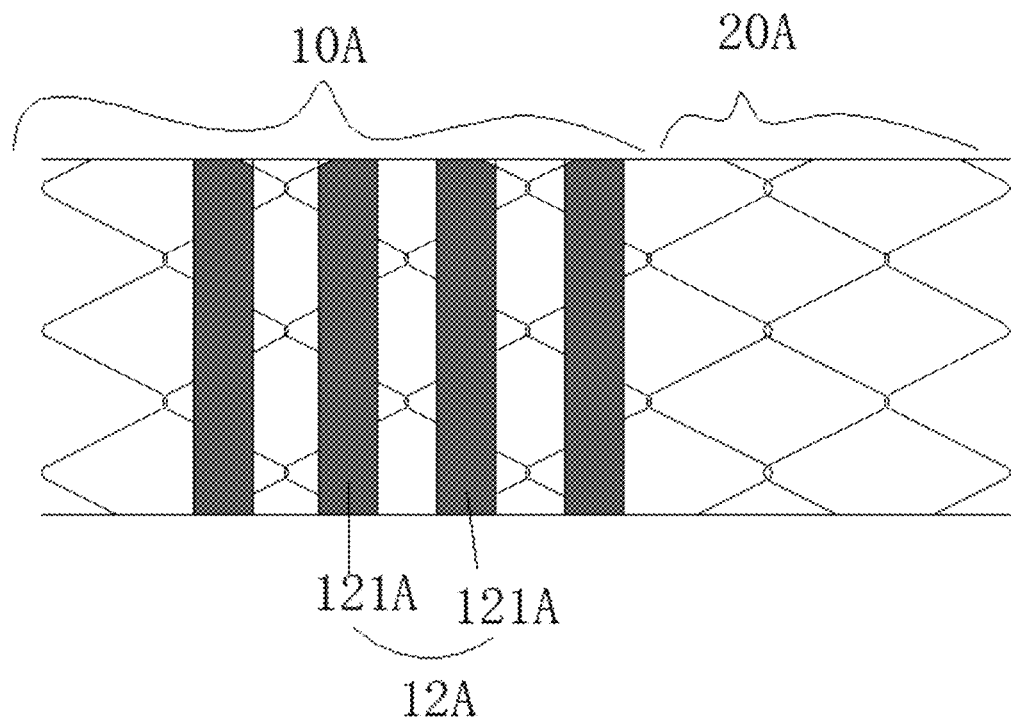
FIG. 12 is a schematic structural diagram of a covered stent according to yet another embodiment of the present invention.

It can be understood that, as shown in FIG. 12, in other embodiments, the plurality of covering film tapes 121A may also achieve covering in a circumferentially surrounding manner, that is, the covering film tapes 121A cover wave rods of the first corrugated rings and are wound circumferentially around the first corrugated rings. The width of each covering film tape is less than the height of the first corrugated ring, thus ensuring that during the covering of the covering film tapes 121A, the crests and troughs of the first corrugated rings are not covered.

Adjacent first corrugated rings of the first section 10A of this embodiment can move axially, so as to better adapt to the shape of the blood vessel. At the same time, since the plurality of second corrugated rings of the second section 20A are fixedly connected, it is ensured that the entire covered stent will not be shortened excessively after the axial movement of the first corrugated rings, thereby ensuring the anchoring capability of the covered stent.

Embodiment V

Figure 13:
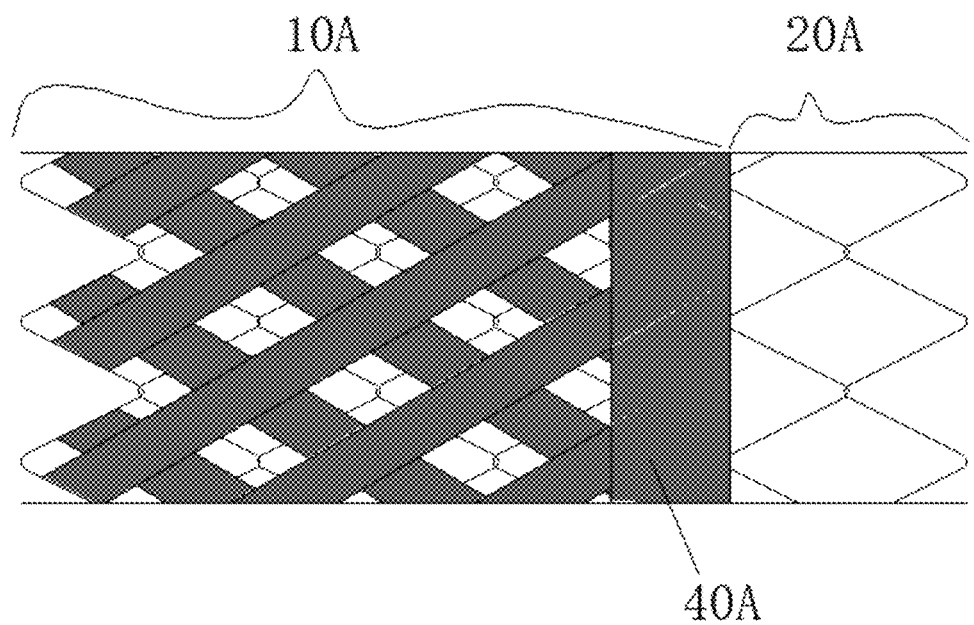
FIG. 13 is a schematic structural diagram of a covered stent according to a further embodiment of the present invention.

As shown in FIG. 13, the covered stent of this embodiment has substantially the same structure as that of the covered stent of Embodiment IV, except that the distal part of the first section 10A of the covered stent of this embodiment further includes a sealing structure 40A. Specifically, the sealing structure 40A is arranged on a part of the distal part of the first section 10A that is connected to the second section 20A. The sealing structure 40A is a sealing film arranged circumferentially around the distal part of the first section 10A, so that the sealing structure 40A protrudes at least partially from the outer surface of the first section 10A.

It can be understood that, in other embodiments, the sealing structure 40A can also be a suture sutured around the wave rod of the first corrugated ring at the most distal end of the first section 10A; that is, the first corrugated ring and an edge of the first covering film are reinforced by the suture, which increases the outer diameter of the distal part of the first section.

Embodiment VI

Referring to FIGS. 1A to 2A, the covered stent 100 of this implementation includes a main body part 10 and a skirt part 20. The main body part 10 is internally hollow and has openings at two opposite ends, and the skirt part 20 is positioned on, and surrounds, an outer side of the main body part 10. The skirt part 20 includes a folding section 21 and a connecting section 22. In a natural state, the distal end of the connecting section 22 is connected to an outer surface of the main body part 10 and forms a first opening 23 facing the proximal end. The folding section 21 includes a connecting end, through which the folding section 21 is connected to a proximal end of the connecting section 22 in a folding manner; the other end of the folding section 21 opposite to the connecting end is a free end. In the natural state, the folding section 21 extends towards the distal end to form a second opening 24 facing the distal end together with the connecting section 22. During delivery, the covered stent is compressed in a sheath tube; both the folding section and the connecting section are in contact with the outer surface of the main body part; the free end of the folding section extends toward the proximal end; that is, both the opening formed by the folding section and the outer surface of the main body part, and the first opening formed by the connecting section, face the proximal end.

It can be understood that since only one end of the connecting section is connected to the main body part, under the action of an external force, the connecting section can also be folded relative to the main body part by using a connecting point as an origin. For example, one end of the connecting section that is connected to the folding part will be folded from the proximal end to the distal end, so that the opening that is formed by the connecting section and faces the proximal end also correspondingly turns into an opening facing the distal end. Therefore, the above description is only a relative structural and positional relationship of each component of the covered stent in its natural state.

The folding section 21 includes a first support member 211 and a fourth covering film 212. The fourth covering film 212 is arranged on a surface of the first support member 211 and is connected to the first support member 211. The thickness of the fourth covering film 212 gradually decreases along a direction from an end of the folding section 21 connected to the connecting section 22 to the free end of the folding section 21, so that in this direction, a circumferential binding force of the fourth covering film to the first support member gradually decreases, and the free end of the folding section 21 can be folded towards the distal end from the delivered state to a trend of recovering the natural state without an external force.

It can be understood that, in other embodiments, in the direction from the distal end of the folding section connected to the connecting section to the free end of the folding section, the fourth covering film can also be changed suddenly. For example, the thickness of only the part of the fourth covering film close to the free end of the folding section is smaller, so that the circumferential binding force to the free end of the first support member is reduced due to the small thickness of the fourth covering film close to the free end, and the folding section is easily folded from the delivered state to the natural state.

Figure 1A:
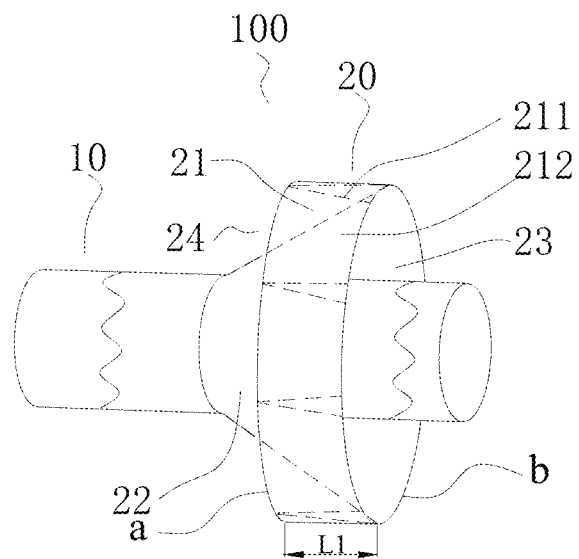
FIG. 1A is a schematic structural diagram of a covered stent of Embodiment VI in a natural state.

As shown in FIG. 1A, in the natural state, the surface of the folding section 21 is parallel or substantially parallel to the surface of the main body part 10; that is, in the natural state, the folding section 21 may extend in the lengthwise direction of the main body part, or may extend inwardly toward the outer surface of the main body part, or extends outwardly away from the outer surface of the main body part. After the folding section 21 is released from the radial binding of the sheath tube, the folding section 21 is gradually folded towards the distal end by taking the end (hereinafter referred to as "connecting end") connected to the connecting section as the origin, finally forming an anchored state as shown in FIG. 2A.

Figure 2A:
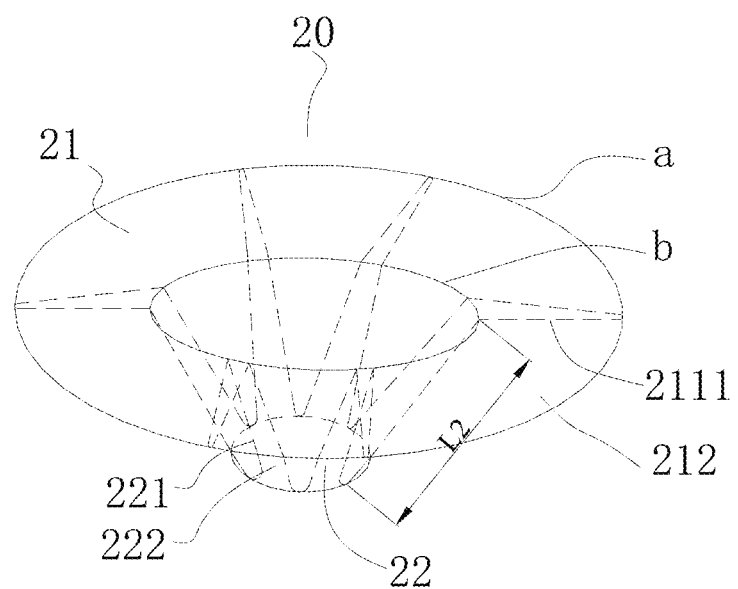
FIG. 2A is a schematic structural diagram of a skirt part, in which a folding section of the covered stent in FIG. 1A is in a folding state.

As shown in FIG. 1A and FIG. 2A, the connecting section 22 has a flared structure, and includes a second support member 221 and a fifth covering film 222. The fifth covering film 222 is arranged on a surface of the second support member 221, and the connecting section 22 is connected to the main body part 10 through the fifth covering film 222. The fourth covering film 212 can enlarge an anchoring area of the folding section 21, and can also prevent the occurrence of endoleak together with the fifth covering film 222.

The first support member 211 and the second support member 221 may respectively include at least one corrugated ring, and the two support members may be connected by mutually hooking the corrugated rings. In this embodiment, the first support member includes a plurality of support rods 2111. Among the plurality of support rods 2111, one end of each of two adjacent support rods 2111 is connected to form a crest, and the other ends of the two adjacent support rods 2111 are connected to form a trough, thereby forming a waveform structure in which a plurality of crests can be regarded as a plurality of free ends, and a plurality of troughs are close to the connecting section. Alternatively, the first support member 211 and the second support member 221 may also be an integrated structure (that is, the first support member and the second support member are different parts of the same corrugated ring). At this time, the first support member can be folded in a shaping manner relative to the second support member without an external force. In addition, the second support member 221 may also be connected to the main body part via suturing, so that the second support member 221 is flared after being connected to the main body part 10.

In the natural state, the width of the folding section 21 in a horizontal direction in FIG. 1A is L1. The length of the connecting section 22 in its own extending direction is L2, preferably 1 cm≤L2+L1≤2 cm, so as to achieve the desired anchoring performance and anti-endoleak performance of the skirt part, and to reduce the blockage from the skirt part to the opening of the adjacent branch vessel after the covered stent 100 is implanted to the main body stent. In addition, when the anti-displacement performance and sealing performance of the covered stent 100 are comprehensively considered, after the covered stent 100 is implanted into the main body stent, it is usually that the connecting section 22 is in contact with the window of the main body stent. In the folding process of the folding section, when the free end of the folding section is in contact with an inner wall of the main body stent, the folding of the folding section is stopped due to the blockage of the inner wall of the main body stent. In other words, when the covered stent 100 is implanted into the main body stent and cooperates with the main body stent, the folding section may not be completely restored to its natural state. In order to enlarge the contact area between the folding section and the inner wall of the main body stent as much as possible, it is preferable that in the natural state, a projection of the free end of the folding section on the outer surface of the main body part overlaps a connecting point of the connecting section and the outer surface of the main body part, or a projection of the free end of the folding section on the outer surface of the main body part is closer to the proximal end of the main body part than the connecting point of the connecting section and the outer surface of the main body part. FIG. 2A shows another preferable state diagram of cooperation with the main body stent after the implantation of the folding section. The folding section 21 is basically fitted to an inner wall of the main body stent and is basically perpendicular to an axial direction of the main body part.

In this implementation, end a (i.e., the distal end of the folding section 21 in the natural state) of the folding section 21 is the free end, and end b (i.e., the proximal end of the folding section 21 in the natural state) of the folding section 21 is connected to the connecting section 22. The distal end of the connecting section 22 is connected to the outer surface of the main body part 10, so as to achieve mutual fixation between the skirt part 20 and the main body part 10. The thickness range of the fourth covering film 212 close to end a is optionally 0.02 mm-0.05 mm. The thickness range of the fourth covering film 212 close to end b is 0.06 mm-0.12 mm. The thickness of the fourth covering film 212 from end a to end b gradually increases. Since the thickness of the fourth covering film 212 on the folding section 21 close to the free end is smaller, the circumferential binding force on the folding section 21 is low, thereby ensuring that the folding section 21 can automatically flip from the delivered state to the natural state without an external force, achieving mutual anchoring between the covered stent 100 and the main body stent 200, and establishing reliable blood supply of a branch vessel.

In this implementation, the fourth covering film of the folding section 21 and the first support member are substantially in the same plane, and the first support member 211 is covered by the fourth covering film 212; that is, an enclosed area between two adjacent support rods is equal to an area of the fourth covering film located between the two adjacent support rods. Furthermore, an edge enclosed by the free end of the first support member overlaps an edge of the fourth covering film. The fourth covering film 212 is annular. The radial length of the fourth covering film 212 is equal to that of the first support member 211, so as to maximize the effective covering area of the fourth covering film 212 and enlarge the anchoring area between the folded folding section 21 and the main body stent 200, thus enhancing the fixing effect of the covered stent 200. As shown in FIG. 3A, in other examples of this embodiment, when the fourth covering film and the first support member are basically in the same plane, the fourth covering film 212 between any adjacent free ends on the first support member 211 is curved towards the proximal end to form an arc shape; that is, the average amount of circumferential coverage close to the free end of the first support member is less than that which is close to the connecting end between the first support member and the connecting section. The average amount of circumferential coverage can be defined as the amount of coverage per unit area on any annular surface. The coverage amount can be determined by the degree of coverage and the thickness of a covering film; that is, when the covering film has the same thickness, in case of complete covering, the coverage amount per unit area is equal. When the covering film has the same thickness, but in the case of incomplete covering, the average amount of circumferential coverage of a ring containing an uncovered part is less than that of the completely covered part. By adopting the design shown in FIG. 3A, the first support member 211 can also be fully wrapped, but the average amount of circumferential coverage close to the free end of the first support member is reduced, thereby reducing the circumferential binding force between the adjacent free ends of the first support members by the fourth covering film, also ensuring the anchoring area and anchoring force of the folded folding section 21, and ensuring the anchoring effect. It can be understood that, in this example, the thickness of the fourth covering film may be uniform, or the thickness of the fourth covering film close to the free end may be less than the thickness of the fourth covering film close to the connecting end.

Figure 4A:
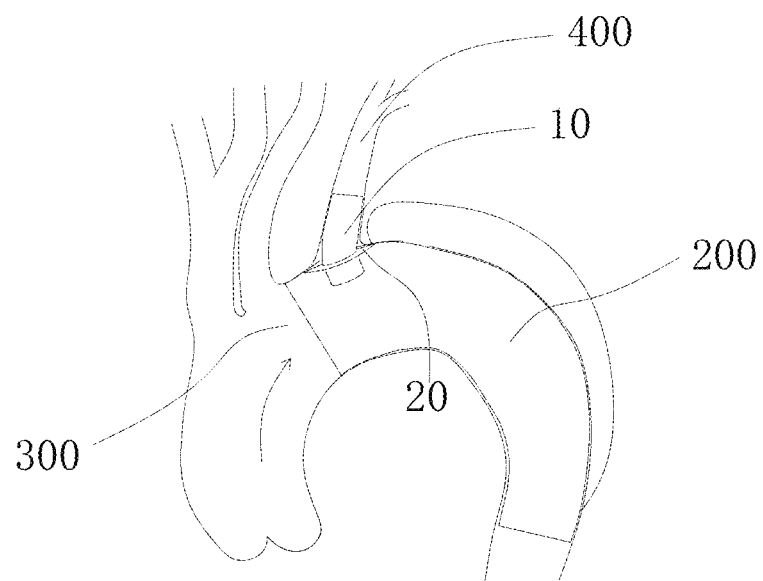
FIG. 4A is a schematic structural diagram of an anchoring state of the covered stent of the present invention and a main body stent.

As shown in FIG. 4A, according to the covered stent 100 of the present invention, when abutment with the main body stent 200 in the aortic vessel 300 is required, the covered stent 100 is implanted via the branch vessel 400 after the main stent 200 creates a window, and cooperates with the main body stent 200. Specifically, after the main body stent 200 creates a window, the proximal end of the main body part 10 of the covered stent 100 is extended into the main body stent 200 via the branch vessel 400 and the created window, so that it is communicated with the main body stent 200 and the branch vessel 400 through the openings in the two ends of the main body part 10, so as to keep the blood flow in the branch vessel 400 unblocked. During the process of implanting the covered stent 100, with the withdrawal of the sheath tube in the delivery system, the folding section is gradually released and folded. The thickness of the fourth covering film 212 on the folding section 21 gradually decreases from the end of the folding section connected to the connecting section to the free end, so that the binding force of the fourth covering film 212 close to the free end to the first support member 211 is low, and folding easily occurs. The folding section 21 of the skirt part 20 can be automatically folded without an external force. In addition, during the process of withdrawing the sheath tube, under the extruding action of an end part of the sheath tube, the folding section 21 can also be assisted in folding; the opening size of the second opening 24 is increased at the same time; the contact area between the folding section 21 and the inner wall of the main body stent at the window position is enlarged (that is, the fitting area of the covered stent 100 at the window position is enlarged), thereby improving the sealing effect and fixing effect of the covered stent 100 at the window position, preventing the covered stent 100 from moving, effectively ensuring the success rate of stent positioning during the surgical process, and reducing the potential safety hazard caused by the movement of the stent. During the process of restoring the folding section from the delivered state to the natural state, without considering the existence of the fourth covering film, the distance between adjacent support rods on the first support member of the folding section varies. When the folding section is perpendicular to the axial direction of the main body part (i.e., the state shown in FIG. 2A), the distance between the support rods is the longest. As long as it is ensured that the folding section can be folded from the delivered state to a transitional state shown in FIG. 2A, the folding section can be folded smoothly. Therefore, by reducing the thickness of the fourth covering film on the folding section close to the free end, the circumferential binding force between the adjacent free ends is reduced to ensure that the folding section can be smoothly folded.

Embodiment VII

Figure 6A:
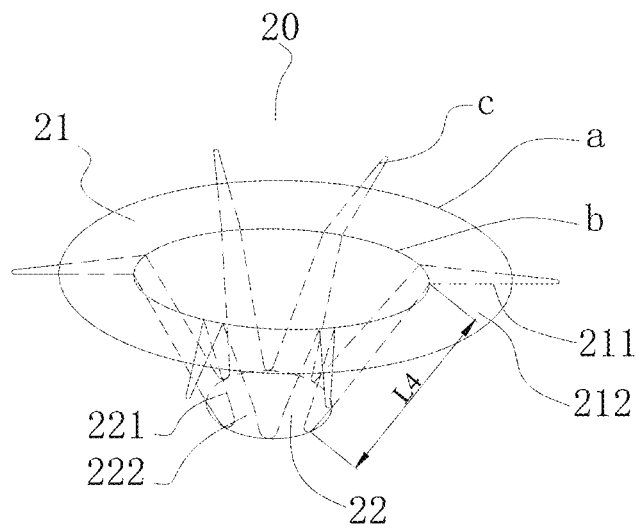
FIG. 6A is a schematic structural diagram of a skirt part, in which a folding section of the covered stent in FIG. 5A is in a folding state.

As shown in FIG. 5A and FIG. 6A, in this embodiment, the entire structure of the covered stent 100 is basically consistent with that in Embodiment VI, except that the fourth covering film 212 of the folding section 21 of this embodiment does not completely cover the first support member. The free end of the first support member 211 is exposed from the fourth covering film 212. In a longitudinal extending direction of the folding section, the length dimension of the fourth covering film 212 is less than that of the first support member 211; that is, the first support member 211 includes an exposed part close to the free end. Thus, the average amount of circumferential coverage close to the free end of the first support member is still less than that which is close to the connecting end between the first support member and the connecting section. In addition, for the exposed free ends of the first support member, no circumferential constraint by the covering film exists between two adjacent free ends, thus the folding section is more easily folded from the delivered state to the natural state. Preferably, the length of the fourth covering film 212 in the radial direction is a half of the length of the first support member 211 in the radial direction; that is, there is no covering film structure on half of the length of the first support member 211 close to the free end. In such a design, the binding force of the fourth covering film 212 to the first support member 211 can be reduced, thus better facilitating the folding section to be folded.

The width of the fourth covering film 212 in the horizontal direction in FIG. 5A is L3, and the length of the connecting section 22 in its own extending direction is L4, preferably 1 cm≤L4+L3≤2 cm, so as to ensure the anchoring performance and anti-endoleak performance of the skirt part, and reduce the blockage from the skirt part to the opening of the adjacent branch vessel after the covered stent 100 is implanted to the main body stent. In addition, like the above embodiment, preferably, in the natural state, a projection of the free end of the folding section on the outer surface of the main body part overlaps a connecting point between the connecting section and the outer surface of the main body part, or a projection of the free end of the folding section on the outer surface of the main body part is closer to the proximal end of the main body part than the connecting point between the connecting section and the outer surface of the main body part. In this embodiment, the thickness of the fourth covering film 212 from end a to end b may also gradually increase. In other examples of this embodiment, the thickness of the fourth covering film may also be uniform.

As shown in FIG. 6A, on the first support member 211, region c is enclosed between the free end of the first support member 211 and an end of the fourth covering film 212 away from the connecting section. In other embodiments, the fourth covering film 212 may also be provided in area c. The fourth covering film 212 in region c and the fourth covering film 212 of the proximal end of the folding section 21 jointly fully cover the area enclosed by the first support member 211, thus further enlarging the anchoring area of the folding section 21. The anchoring force is ensured, and the folding performance of the folding section 21 will not be affected.

Figure 7A:
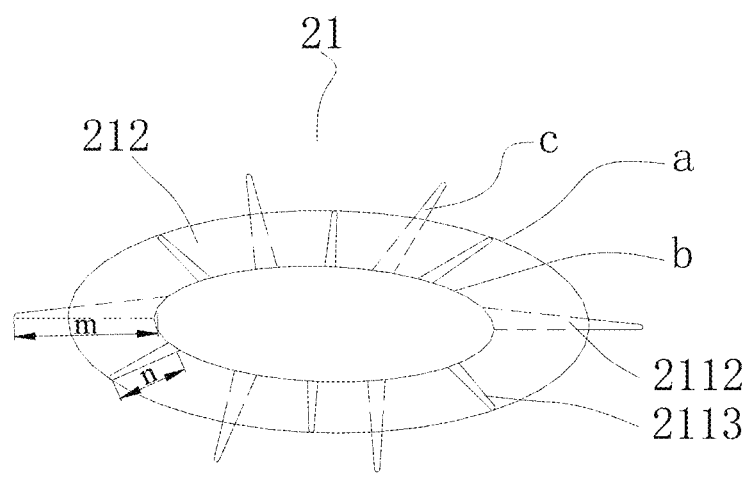
FIG. 7A is a schematic structural diagram of a folding section in a folding state according to another example in Embodiment VII.

As shown in FIG. 7A, in other examples of this embodiment, the support rod 2111 includes a plurality of long support rods 2112 and short support rods 2113. The length of the short support rod 2113 is less than that of the long support rod 2112. Two adjacent short support rods form a low crest, and two adjacent long support rods form a high crest. The high crests and the low crests are disposed alternately. The low crests are closer to the connecting section than the high crests, and the fourth covering films 212 are provided on areas where the short support rods 2113 are located.

The length of the long support rod 2112 is denoted as m, and the length of the short support rod 2113 is denoted as n, m>n, so that the covering area of the fourth covering film 212 just covers an end surface of the short support rod 2113. Preferably, m≥2n; in this way, both the support performance and sealing performance of the folding section can be considered. By adding the short support rod 2113, the supporting force of the folded folding section 21 can be further improved, and the anchoring force between the folded folding section 21 and an anchored region can be improved. Further, for the folding section 21 in this example, the fourth covering film 212 can also be provided in region c enclosed by the part of the first support member 211 extending out of the fourth covering film 212, and the fourth covering film 212 in region c and the fourth covering film 212 of the proximal end of the folding section 21 jointly fully cover the region enclosed by the first support member 211, thus further enlarging the anchoring area of the fourth covering film 212 in the folding section 21, and reducing the local pressure caused by the folding section on the main body stent, so that the anchoring force is ensured, and the folding performance of the folding section 21 will not be affected.

Embodiment VIII

Figure 8A:
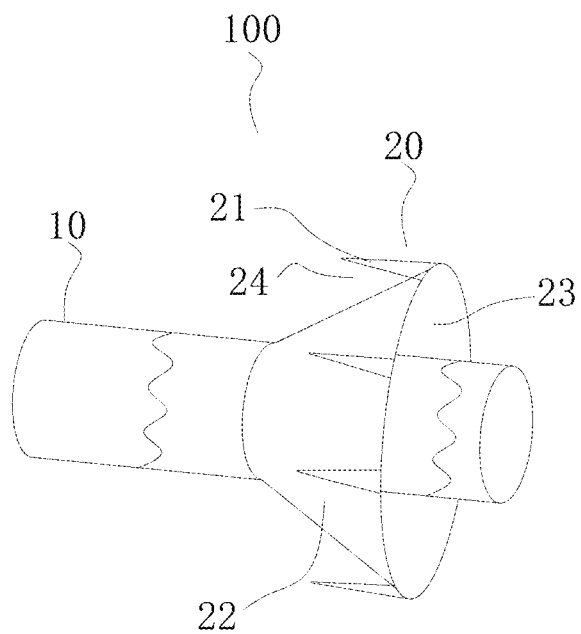
FIG. 8A is a schematic structural diagram of a covered stent of Embodiment VIII in a natural state.

Referring to FIG. 8A and FIG. 9A, the covered stent 100 in this embodiment includes a main body part 10 and a skirt part 20. The main body part 10 is internally hollowed and has openings at two ends. The skirt part 20 is positioned outside and surrounds the main body part 10. The skirt part 20 includes a folding section 21 and a connecting section 22. A distal end of the connecting section 22 is connected with the main body part 10 and forms a first opening 23 facing a proximal end. The folding section 21 is connected with the proximal end of the connecting section 22 in a foldable manner. A second opening 24 facing the distal end is formed between the folding section 21 and the connecting section 22. The connecting section 22 includes a second support member 221 and a covering film 222, and the covering film 222 is disposed on a surface of the second support member 221 and is connected to the second support member 221. The folding section 21 includes a first support member 211. In a natural state, a proximal end of the first support member 211 is connected with a proximal end of the second support member 221, and a distal end of the first support member 211 extends toward the distal end to form a free end. The covering film 222 extends from the distal end of the second support member 221 to the proximal end of the second support member 221 and does not exceed the proximal end of the first support member 211. A difference from Embodiment VI is that in this embodiment, the first support member 211 of the folding section 21 is not provided with a fourth covering film, that is, the first support member 211 is completely exposed. The first support member 211 is not provided with a fourth covering film, so that the first support member 211 is completely unconstrained by a covering film, so that it is easier to fold. In other examples, a fourth covering film 211 may also be provided in region c between the free end of the first support member 211 and an end of a fifth covering film away from an outer surface of a main body tube of the folding section 21, and is connected with the covering film 222 on the connecting section 22 to form a covering film region. The covering film added in region c can prevent endoleak between the first support member 211 and the second support member 221, and at the same time, enlarge the anchoring area between the folded folding section 21 and the anchored region. The anchoring force is increased, and the folding performance of the folding section 21 will not be affected.

In addition, like the above embodiment, preferably, in the natural state, a projection of the free end of the folding section on the outer surface of the main body part overlaps a connecting point between the connecting section and the outer surface of the main body part, or a projection of the free end of the folding section on the outer surface of the main body part is closer to the proximal end of the main body part than the connecting point between the connecting section and the outer surface of the main body part.

Embodiment IX

Figure 11A:
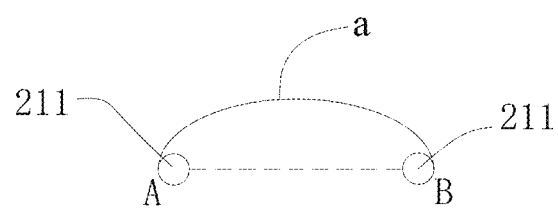
FIG. 11A is a partial schematic sectional structural diagram of the folding section in FIG. 10A.

As shown in FIG. 10A to FIG. 12A, the overall structure of the covered stent 100 in this embodiment is basically the same as that in Embodiment VI, and a difference from Embodiment VI is that in this embodiment, the fourth covering film 212 between any two adjacent crests on the first support member 211 is outwardly bulged or inwardly sunken relative to a plane formed by the two adjacent crests; that is, the fourth covering film is connected to the first support member, but they are not completely in the same plane. As shown in FIG. 11A, in this embodiment, the fourth covering film 212 between end point A and end point B on the adjacent support rods of the first support member 211 is extends in a convex manner toward the outer side and forms end a. Through the convex arrangement, in particular, the length of the fourth covering film between the adjacent support rods close to the free end of the first support member is greater than a linear distance between the adjacent support rods, so that the circumferential binding force of the fourth covering film between the support rods is low, and the convex fourth covering film 212 in this embodiment is easier to fold than the flat fourth covering film 212.

As shown in FIG. 12A, in other examples, the fourth covering film 212 between end point A and end point B on two adjacent support rods on the first support member 211 can also be concave toward the outer side and form end a.

It can be understood that, in other examples, one part of the fourth covering film between adjacent support rods may be sunken inwardly, one part of the fourth covering film is bulged outwardly, and one part of the fourth covering film is in the same plane as the support rods.

It can be understood that, in order to provide the fourth covering film 212 of the folding section 21 with a concave or convex structure during preparation of the folding section 21 of this embodiment, an original covering film can be spread on the basis of manufacturing the original covering film (that is, after covering is completed, the original covering film between the support rods is in a tensioned state), so that after the original covering film slightly deforms, the fourth covering film is formed. The surface area of the fourth covering film is larger than that of the original covering film, and the thickness of the fourth covering film 212 between end points A and B is also reduced, that is, the average circumferential thickness of the fourth covering film 212 close to the free end of the folding section 21 is less than the thickness of the fourth covering film 212 on the remaining parts of the folding section 21, so that a convex or concave structure is formed. An actual length of the distal edge of the fourth covering film 212 between end point A and end point B is greater than the linear distance between the end point A and the end point B. It can be understood that before the fourth covering film is spread, the thickness of the covering film may be uniform or gradually decrease from the free end to the connection. It can also be understood that the bulge or recess of the fourth covering film can also be realized by cooperation with other molds, that is, after the covering is completed, the thickness of the fourth covering film is still uniform.

It should be understood that the sealing structure of this embodiment is applicable to covered stents of other embodiments of the present invention, and details are not repeated here.

In this embodiment, by disposing the sealing structure 40A at the distal part of the first section, the sealing effect of the distal end of the first section 10A can be further improved to avoid endoleak after blood flows out of the window of the second section 20A.

The above descriptions are only preferred specific implementation modes of the present invention, but the protection scope of the present invention is not limited to this. Changes or substitutions that can be easily considered by any person skilled in the art without departing from the technical scope disclosed by the present invention shall all fall within the protection scope of the present invention. Therefore, the protection scope of the present invention should be subject to the protection scope of the claims.

The invention claimed is:

1. A covered stent, comprising a mesh-shaped support structure, further comprising a first section and a second section connected to a proximal end or a distal end of the first section, wherein the first section comprises a plurality of first corrugated rings, and a first covering film which covers surfaces of the first corrugated rings; the second section comprises a plurality of second corrugated rings, two adjacent second corrugated rings are fixedly connected through a connector; a plurality of windows are formed between the plurality of second corrugated rings; and the plurality of first corrugated rings and the plurality of second corrugated rings form the support structure; a surface of each second corrugated ring is wrapped with a protecting film; the connectors and the protecting films both comprise macromolecular materials; and the connectors are fused with the protecting films; wherein the covered stent comprises a sealing film arranged circumferentially around a distal part of the first section; and the sealing film at least partially protrudes from an outer surface of the first section; wherein the first film comprises a plurality of covering film tapes, and each of the first corrugated rings has a crest and a trough, wherein at least two of the adjacent first corrugated rings are connected by hooking crests and troughs of the adjacent first corrugated rings to form crest-trough hooking positions, the plurality of covering film tapes form a plurality of blank regions, and outer surfaces of the crest-trough hooking positions are exposed in the blank regions.

2. The covered stent according to claim 1, wherein the second section comprises a hollow stent section; the hollow stent section comprises a plurality of hollow structures; edges of the hollow structures are consistent with waveform edges of the second corrugated rings; and the hollow structures form the windows.

3. The covered stent according to claim 1, wherein the second section further comprises a second covering film; the second covering film covers surfaces of the plurality of second corrugated rings; the plurality of second corrugated rings are fixedly connected through the covering film; the second covering film is provided with a plurality of through holes; and the through holes form the windows.

4. The covered stent according to claim 3, wherein the second covering film comprises an outer-layer covering film and an inner-layer covering film; the outer-layer covering film and the inner-layer covering film are fused into a whole via thermal treatment; and the second corrugated rings are fixed between the outer-layer covering film and the inner-layer covering film.

5. The covered stent according to claim 1, wherein the covered stent further comprises a third section; the third section is positioned outside and surrounds the first section; a distal end of the third section is connected to the outer surface of the first section; a proximal end of the third section forms an opening facing the proximal end; and the third section comprises a third corrugated ring and a third covering film covering a surface of the third corrugated ring.

6. The covered stent according to claim 5, wherein a corrugated ring diameter of the third corrugated ring is greater than a diameter of each first corrugated ring, and a waveform structure of the first corrugated ring is substantially the same as that of the third corrugated ring; and the wave number of the first corrugated ring is less than that of the third corrugated ring.

7. The covered stent according to claim 5, wherein a proximal corrugated ring of the third section and the first corrugated ring which is radially opposite to the proximal corrugated ring on the first section have staggered crests.

8. The covered stent according to claim 5, wherein the third section includes a folding section and a connecting section, one end of the connecting section is connected with the first section and forms the opening facing the proximal end of the first section; the folding section includes a connecting end and an other end; the connecting end of the folding section is connected to the other end of the connecting section, and the other end of the folding section opposite to the connecting end forms a free end; wherein in a natural state, the folding section extends toward a distal end of the first section and forms an opening facing the distal end of the first section together with the connecting section; the folding section includes a first support member, and a fourth covering film arranged on the first support member and connected to the first support member.

9. The covered stent according to claim 8, wherein the thickness of the fourth covering film gradually decreases along a direction from the connecting end of the folding section to the free end.

10. The covered stent according to claim 8, wherein the first support member and the fourth covering film are on the same plane; and the first support member includes a plurality of support rods.

11. The covered stent according to claim 10, wherein each support rod includes a long support rod and a short support rod; two adjacent short support rods are connected to form a low crest; two adjacent long support rods are connected to form a high crest; the lows crests and the high crests are alternately arranged; the low crests are closer to the connecting section than the high crests; the short support rods are all covered by the fourth covering film; and the long support rods are partially exposed.

12. The covered stent according to claim 8, wherein in a longitudinal extending direction of the folding section, the length dimension of the first support member is greater than that of the fourth covering film; and the free end of the first support member is exposed to the outside.

13. The covered stent according to claim 8, wherein the first support member and the fourth covering film are not completely in the same plane; and on the fourth covering film close to the free end, at least a part of the fourth covering film is outwardly bulged or inwardly sunken relative to a plane where the first support member is located.

14. The covered stent according to claim 8, wherein the connecting section includes a second support member and a covering film; the covering film is arranged on a surface of the second support member and is connected to the second support member; in a natural state, a proximal end of the first support member is connected to a proximal end of the second support member; and the covering film extends from the distal end of the second support member to the proximal end of the second support member and does not exceed the proximal end of the first support member.

15. The covered stent according to claim 14, wherein in the natural state, a projection of the free end of the folding section on the outer surface of the main body part overlaps a connecting point between the connecting section and the outer surface of the main body part.

16. The covered stent according to claim 1, wherein the plurality of covering film tapes are intersected with each other and the plurality of blank regions are defined in an interstice between the plurality of covering film.

17. The covered stent according to claim 1, wherein the plurality of covering film tapes surround the first corrugated first rings, the adjacent first corrugated first rings are spaced-apart, and the blank region is defined in an interstice between the adjacent covering film tapes.

18. A covered stent, comprising a mesh-shaped support structure, further comprising a first section and a second section connected to a proximal end or a distal end of the first section, wherein the first section comprises a plurality of first corrugated rings, and a first covering film which covers surfaces of the first corrugated rings; the second section comprises a plurality of second corrugated rings, two adjacent second corrugated rings are fixedly connected through a connector; a plurality of windows are formed between the plurality of second corrugated rings; and the plurality of first corrugated rings and the plurality of second corrugated rings form the support structure; a surface of each second corrugated ring is wrapped with a protecting film; the connectors and the protecting films both comprise macromolecular materials; and the connectors are fused with the protecting films; wherein the covered stent comprises a sealing film arranged circumferentially around a distal part of the first section; the sealing film at least partially protrudes from an outer surface of the first section; and wherein a crest of one second corrugated ring is connected to a trough to an adjacent second corrugated ring by hanging, and wherein the connector winds the crest of one second corrugated ring and the trough of the adjacent second corrugated ring.

\* \* \* \* \*